US006929796B1

(12) United States Patent  
Conti-Fine

(10) Patent No.: US 6,929,796 B1  
(45) Date of Patent: Aug. 16, 2005

(54) METHODS TO TREAT UNDESIRABLE IMMUNE RESPONSES

(75) Inventor: Bianca M. Conti-Fine, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 08/991,143

(22) Filed: Dec. 16, 1997

Related U.S. Application Data

(63) Continuation-in-part of application No. 08/564,972, filed on Nov. 30, 1995, now Pat. No. 5,843,462.

(51) Int. Cl.$^7$ .............................................. A61K 38/00
(52) U.S. Cl. ..................................... 424/185.1; 514/13
(58) Field of Search ...................... 424/185.1, 274.1, 424/275.1; 514/2; 530/300, 303, 380, 395, 399, 841, 842, 868

(56) References Cited

U.S. PATENT DOCUMENTS

| | | | |
|---|---|---|---|
| 4,649,132 A | 3/1987 | Zimmerman et al. | 514/12 |
| 4,822,606 A | 4/1989 | Snyderman et al. | 424/88 |
| 4,962,091 A | 10/1990 | Eppstein et al. | 514/2 |
| 5,114,721 A | 5/1992 | Cohen et al. | 424/534 |
| 5,158,884 A | 10/1992 | Conti-Tronconi et al. | 435/240.2 |
| 5,298,490 A | 3/1994 | Heavner et al. | 514/17 |
| 5,571,499 A | 11/1996 | Hafler et al. | 414/43 |
| 5,571,500 A | 11/1996 | Hafler et al. | 424/43 |
| 5,578,496 A | 11/1996 | Atassi et al. | 436/506 |
| 5,585,362 A | 12/1996 | Wilson et al. | 514/44 |
| 5,614,396 A | 3/1997 | Bradley et al. | 435/172.3 |
| 5,641,473 A | 6/1997 | Hafler et al. | 424/43 |
| 5,641,474 A | 6/1997 | Hafler et al. | 424/43 |
| 5,681,571 A | 10/1997 | Holmgren et al. | 424/236.1 |
| 5,785,973 A | 7/1998 | Bixler et al. | 424/196.11 |
| 5,817,308 A * | 10/1998 | Scott et al. | |
| 6,077,509 A * | 6/2000 | Weiner et al. | 424/184.1 |
| 6,106,844 A * | 8/2000 | King | 424/275.1 |
| 6,268,491 B1 * | 7/2001 | Garman et al. | |

FOREIGN PATENT DOCUMENTS

| | | | |
|---|---|---|---|
| EP | 0378881 | 1/1989 | H04K/7/00 |
| WO | 88/10120 | 12/1988 | A61K/39/00 |
| WO | 92/06117 | 4/1992 | C07K/15/00 |
| WO | 94/25060 | 4/1993 | A61K/37/38 |
| WO | WO 94/00148 * | 1/1994 | |
| WO | 95/26365 | 10/1995 | C07K/19/00 |
| WO | 97/19698 | 11/1995 | A61K/39/44 |

OTHER PUBLICATIONS

Daniel et al., PNAS vol. 93 pp. 956–960, 1996.*
Wraith et al. Cell. vol. 59:247–255, 1989.*
Tisch et al. PNAS vol. 91:437–438, 1994.*
Karin et al. J. Exp Med. vol. 180:2227–2237, 1994.*
Kurup et al. Peptides, vol. 17. 183–190, 1996, 1996.*
Norman, P. S. et al. Amer. J. Respir. Crit. Care Med. 154 (6 Pt 1):1623–1628, Dec. 1996.*
Moiola, L. et al. J. Immunol. 152 (9): 4686–4698, May 1994.*
Hetzel, C. et al. Int. Arch. Allergy Immunol. 107 (1–3): 275–277, May–Jun. 1995.*
Protti, M.P., et al., "Myasthenia Gravis: Recognition of a Human Autoantigen at the Molecular Level", *Immunol. Today*, 14, pp. 363–368, (1993).
Higgins, J.A., et al., "Peptide–induced nonresponsiveness of HLA–DP restricted human T cells reactive with Dermatophagoides spp. (house dust mite)", *The Journal of Allergy and Clinical Immunology*, 90 (5), pp. 749–756, (Nov. 1992).
Briner, T.J., et al., "Peripheral T–cell Tolerance Induced in Naive and Primed Mice by Subcutaneous Injection of Peptides from the Major Cat Allergen Fel d I", *Proc. Natl. Acad. Sci. USA*, 90, 7608–7612 (1993).
Conti–Fine, B.M., "T–Cell Recognition of the Acetylcholine Receptor in Myasthenia Gravis", $IX^{th}$ *International Conference on Myasthenia Gravis and Related Disorders*, Santa Monica, California, Abstract (May 7–10, 1997).
Counsell, C.M., et al., "Allergens, IgE, Mediators, Inflammatory Mechanisms. Definition of the Human T–Cell Epitopes of Fel d 1, the Major Allergen of the Domestic Cat", *J. Allergy Clin. Immunol.*, 98(5), 884–894 (1996).
Good, M.F., et al., "Peptide Immunization Can Elicit Malaria Protein–Specific Memory Helper but Not Proliferative T Cells", *Peptide Research*, 3(3), 110–115 (1990).
Hoyne, G.F., et al., "Inhibition of T Cell and Antibody response to House Dust Mite Allergen by Inhalation of the Dominant T Cell Epitope in Naive and Sensitized Mice", *J. Exp. Med.*, 178, 1783–1788 (1993).
Lennon, V.A., et al., "Definition of Myasthenogenic Sites of the Human Acetylcholine Receptor Using Synthetic Peptides", *Annals of the New York Academy of Sciences*, 505, 439–450 (1987).
Lennon, V.A., et al., "Region of Peptide 125–147 of Acetylcholine Receptor α Subunit is Exposed at Neuromuscular Junction and Induces Experimental Autoimmune Myasthenia Gravis, T–cell Immunity, and Modulating Antibodies", *Proc. Natl. Acad. Sci. USA*, 82, 8805–8809 (1985).
Shaw, D.M., et al., "Influence of the T–Helper Epitope on the Titre and Affinity of Antibodies to B–Cell Epitopes after Co–Immunization", *Molecular Immunology*, 30(11), 961–968 (1993).

(Continued)

*Primary Examiner*—Patrick J. Nolan
(74) *Attorney, Agent, or Firm*—Schwegman, Lundberg, Woessner & Kluth, P.A.

(57) ABSTRACT

Isolated and purified peptides and variants thereof, useful to prevent or treat antibody-mediated diseases, or indications caused by an undesirable antibody response to a given antigen, are provided. Also provided are peptides and methods useful to prevent or treat indications associated with the use of viral vectors in gene replacement therapy. Further, a method to inhibit or prevent aberrant immune responses to exogenous, non-infectious antigen is provided.

18 Claims, 10 Drawing Sheets-

OTHER PUBLICATIONS

Bellone, M., et al., "Experimental Myasthenia Gravis in Congenic Mice. Sequence Mapping and H–2 Restriction of T Helper Epitopes of the α Subunits of *Torpedo californica* and Murine Acetylcholine Receptors", *Eur. J. Immunol., 21*, 2303–2310 (1991).

Conti–Fine, B.M., et al., In: *Myasthenia Gravis: The Immunobiology of an Autoimmune Disease*, R.G. Landers Co., Austin, TX, p. 89–104, 121–147, 149–206 (1997).

Conti–Fine, B.M., et al., "Antibodies as Tools to Study the Structure of Membrane Proteins: The Case of the Nicotinic Acetylcholine Receptor", *Annual Review of Biophysics and Biomolecular Structure, 25*, 197–229 (1996).

Karpati, G., et al., "The Scope of Gene Therapy in Humans: Scientific, Safety and Ethical Considerations", *Neuromuscular Disorders, 7*, 273–276 (1997).

Karpus, W.J., et al., "Inhibition of Relapsing Experimental Autoimmune Encephalomyelitis in SJL Mice by Feeding the Immunodominant PLP139–151 Peptide", *Journal of Neuroscience Research, 45*, 410–423 (1996).

Lider, O., et al., "Suppression of Experimental Autoimmune Encephalomyelitis by Oral Adminstration of Myelin Basic Protein. II. Supression of Disease and in Vivo Immune Responses Is Mediated by Antigen–Specific $CD8^+T$ Lymphocytes", *The Journal of Immunology, 142*, 748–752 (Feb. 1, 1989).

Ma, C.–G., et al., "Suppression of Experimental Autoimmune Myasthenia Gravis by Nasal Adminstration of Acetylcholine Receptor", *Journal of Neuroimmunology, 58*, 51–60 (1995).

Metzler, B., et al., "Inhibition of Experimental Autoimmune Encephalomyelitis by Inhalation but not Oral Adminstration of the Encephalitogenic Peptide: Influence of MHC Binding Affinity", *International Immunology, 5*, 1159–1165 (1993).

Neutra, M.R., et al., "Antigen Sampling Across Epithelial Barriers and Induction of Mucosal Immune Responses", *Annual Review of Immunology, 14*, 275–300 (1996).

O'Sullivan, D., et al., "Characterization of the Specificity of Peptide Binding to Four DR Haplotypes", *The Journal of Immunology, 145*, 1799–1808 (Sep. 15, 1990).

Phillips, G., et al., "American Society for Blood and Marrow Transplantation Guidelines for Clinical Centers", *Biology of Blood and Marrow Transplantations, 1*, 54–55 (1995).

Schwartz, R.S., et al., "Autoimmunity and Autoimmune Diseases", In: *Fundamental Immunology, Second Edition*, Paul, W.E., (ed.), Raven Press, New York, 819–859 (1989).

Wang, Z.–Y., et al., "Th1 Epitope Repertoire on the α Subunit of Human Muscle Acetylcholine Receptor in Myasthena Gravis", *Neurology, 48*, 1643–1653 (1997).

Weiner, H.L., et al., "Oral Tolerance: Immunologic Mechanisms and Treatment of Animal and Human Organ–Specific Autoimmune Diseases by Oral Administration of Autoantigens", *Annual Review of Immunology, 12*, 809–837 (1994).

Yu, M., et al., "A Predictable Sequential Determinant Spreading Cascade Invarible Accompanies Progression of Experimental Autoimmune Encephalomyelitis: A Basis for Peptide–Specific Therapy After Onset of Clinical Disease", *J. Exp. Med, 183*, 1777–1788 (Apr. 1996).

Shenoy, M., et al., "Suppression of Experimental Autoimmune Myasthenia Gravis by Epitope–Specific Neonatal Tolerance to Synthetic Region α146–162 of Acetylcholine Receptor", *Clinical Immunology and Immunopathology, 66*, 230–238 (Mar. 1993).

Shenoy, M., et al., "The Pathogenic Role of Acetylcholine Receptor α Chain Epitope within α146–162 in the Development of Experimental Autoimmune Myasthenia Gravis in C57BL6 Mice", *Clinical Immunology and Immunopathology, 73*, 338–343 (Dec. 1994).

Yeh, T.–M., et al., "T Cells Reactive with a Small Synthetic Peptide of the Acetylcholine Receptor Can Provide Help for a Clonotypically Heterogeneous Antibody Response and Subsequently Impaired Muscle Function", *The Journal of Immunology, 144*, 1654–1660 (Mar. 1, 1990).

* cited by examiner

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 9

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

FIG. 10

SEQUENCE LISTING

<160> NUMBER OF SEQ ID NOS: 3

<210> SEQ ID NO 1
<211> LENGTH: 1667
<212> TYPE: DNA
<213> ORGANISM: Homo sapiens

<400> SEQUENCE: 1

```
aagcacaggc caccactctg ccctggtcca cacaagctcc ggtagcccat ggagccctgg      60
cctctcctcc tgctctttag cctttgctca gctggcctcg tcctgggctc cgaacatgag     120
acccgtctgg tggcaaagct atttaaagac tacagcagcg tggtgcggcc agtggaagac     180
caccgccagg tcgtggaggt caccgtgggc ctgcagctga tacagctcat caatgtggat     240
gaagtaaatc agatcgtgac aaccaatgtg cgtctgaaac agcaatgggt ggattacaac     300
ctaaaatgga atccagatga ctatggcggt gtgaaaaaaa ttcacattcc ttcagaaaag     360
atctggcgcc cagaccttgt tctctataac aatgcagatg gtgactttgc tattgtcaag     420
ttcaccaaag tgctcctgca gtacactggc cacatcacgt ggacacctcc agccatcttt     480
aaaagctact gtgagatcat cgtcacccac tttcccttttg atgaacagaa ctgcagcatg     540
aagctgggca cctggaccta cgacggctct gtcgtggcca tcaacccgga aagcgaccag     600
ccagacctga gcaacttcat ggagagcggg gagtgggtga tcaaggagtc ccggggctgg     660
aagcactccg tgacctattc ctgctgcccc gacacccct acctggacat cacctaccac     720
ttcgtcatgc agcgcctgcc cctctacttc atcgtcaacg tcatcatccc ctgcctgctc     780
ttctccttct taactggcct ggtattctac ctgcccacag actcagggga gaagatgact     840
ctgagcatct ctgtcttact gtctttgact gtgttccttc tggtcatcgt ggagctgatc     900
ccctccacgt ccagtgctgt gcccttgatt ggaaaataca tgctgttcac catggtgttc     960
gtcattgcct ccatcatcat cactgtcatc gtcatcaaca cacaccaccg ctcacccagc    1020
acccatgtca tgcccaactg ggtgcggaag gtttttatcg acactatccc aaatatcatg    1080
tttttctcca caatgaaaag accatccaga gaaaagcaag acaaaaagat ttttacagaa    1140
gacattgata tctctgacat ttctggaaag ccagggcctc cacccatggg cttccactct    1200 ccctgatca aacacccga ggtgaaaagt gccatcgagg gcatcaagta catcgcagag    1260
accatgaagt cagaccagga gtctaacaat gcggcggcag agtggaagta cgttgcaatg    1320
gtgatggacc acatactcct cggagtcttc atgcttgttt gcatcatcgg aaccctagcc    1380
gtgtttgcag gtcgactcat tgaattaaat cagcaaggat gagcagaaaa tgagctgagc    1440
ttagctctgc cctggaacct accagagcag agaagggcag gagaggaaga tttgtctact    1500
tgctccactc gcacttatca aacgtgttat attccatact tattattgat gataagattt    1560
```

```
acctttatgt aagtttatgg ccttgaagtg ttttcatatt gcttctccct ttagttctgc    1620
tgtctccctg aagagtgaac cctctttagt aaatgaaact aatcact                 1667
```

<210> SEQ ID NO 2
<211> LENGTH: 457
<212> TYPE: PRT
<213> ORGANISM: Homo sapiens

<400> SEQUENCE: 2

```
Met Glu Pro Trp Pro Leu Leu Leu Phe Ser Leu Cys Ser Ala Gly
 1               5                  10                  15

Leu Val Leu Gly Ser Glu His Glu Thr Arg Leu Val Ala Lys Leu Phe
                20                  25                  30

Lys Asp Tyr Ser Ser Val Val Arg Pro Val Glu Asp His Arg Gln Val
            35                  40                  45

Val Glu Val Thr Val Gly Leu Gln Leu Ile Gln Leu Ile Asn Val Asp
        50                  55                  60

Glu Val Asn Gln Ile Val Thr Thr Asn Val Arg Leu Lys Gln Gln Trp
65                  70                  75                  80

Val Asp Tyr Asn Leu Lys Trp Asn Pro Asp Asp Tyr Gly Gly Val Lys
                85                  90                  95

Lys Ile His Ile Pro Ser Glu Lys Ile Trp Arg Pro Asp Leu Val Leu
            100                 105                 110

Tyr Asn Asn Ala Asp Gly Asp Phe Ala Ile Val Lys Phe Thr Lys Val
        115                 120                 125

Leu Leu Gln Tyr Thr Gly His Ile Thr Trp Thr Pro Pro Ala Ile Phe
    130                 135                 140

Lys Ser Tyr Cys Glu Ile Ile Val Thr His Phe Pro Phe Asp Glu Gln
145                 150                 155                 160

Asn Cys Ser Met Lys Leu Gly Thr Trp Thr Tyr Asp Gly Ser Val Val
                165                 170                 175

Ala Ile Asn Pro Glu Ser Asp Gln Pro Asp Leu Ser Asn Phe Met Glu
            180                 185                 190

Ser Gly Glu Trp Val Ile Lys Glu Ser Arg Gly Trp Lys His Ser Val
        195                 200                 205

Thr Tyr Ser Cys Cys Pro Asp Thr Pro Tyr Leu Asp Ile Thr Tyr His
    210                 215                 220

Phe Val Met Gln Arg Leu Pro Leu Tyr Phe Ile Val Asn Val Ile Ile
225                 230                 235                 240

Pro Cys Leu Leu Phe Ser Phe Leu Thr Gly Leu Val Phe Tyr Leu Pro
                245                 250                 255

Thr Asp Ser Gly Glu Lys Met Thr Leu Ser Ile Ser Val Leu Leu Ser
            260                 265                 270

Leu Thr Val Phe Leu Leu Val Ile Val Glu Leu Ile Pro Ser Thr Ser
        275                 280                 285

Ser Ala Val Pro Leu Ile Gly Lys Tyr Met Leu Phe Thr Met Val Phe
    290                 295                 300

Val Ile Ala Ser Ile Ile Ile Thr Val Ile Val Ile Asn Thr His His
305                 310                 315                 320

Arg Ser Pro Ser Thr His Val Met Pro Asn Trp Val Arg Lys Val Phe
                325                 330                 335

Ile Asp Thr Ile Pro Asn Ile Met Phe Phe Ser Thr Met Lys Arg Pro
            340                 345                 350

Ser Arg Glu Lys Gln Asp Lys Lys Ile Phe Thr Glu Asp Ile Asp Ile
```

```
                355                 360                 365
Ser Asp Ile Ser Gly Lys Pro Gly Pro Pro Met Gly Phe His Ser
    370                 375                 380
Pro Leu Ile Lys His Pro Glu Val Lys Ser Ala Ile Glu Gly Ile Lys
385                 390                 395                 400
Tyr Ile Ala Glu Thr Met Lys Ser Asp Gln Glu Ser Asn Asn Ala Ala
                405                 410                 415
Ala Glu Trp Lys Tyr Val Ala Met Val Met Asp His Ile Leu Leu Gly
            420                 425                 430
Val Phe Met Leu Val Cys Ile Ile Gly Thr Leu Ala Val Phe Ala Gly
        435                 440                 445
Arg Leu Ile Glu Leu Asn Gln Gln Gly
    450                 455

<210> SEQ ID NO 3
<211> LENGTH: 437
<212> TYPE: PRT
<213> ORGANISM: Torpedo californica

<400> SEQUENCE: 3

Ser Glu His Glu Thr Arg Leu Val Ala Asn Leu Leu Glu Asn Tyr Asn
1               5                   10                  15
Lys Val Ile Arg Pro Val Glu His His Thr His Phe Val Asp Ile Thr
                20                  25                  30
Val Gly Leu Gln Leu Ile Gln Leu Ile Ser Val Asp Glu Val Asn Gln
            35                  40                  45
Ile Val Glu Thr Asn Val Arg Leu Arg Gln Gln Trp Ile Asp Val Arg
        50                  55                  60
Leu Arg Trp Asn Pro Ala Asp Tyr Gly Gly Ile Lys Lys Ile Arg Leu
65                  70                  75                  80
Pro Ser Asp Asp Val Trp Leu Pro Asp Leu Val Leu Tyr Asn Asn Ala
                85                  90                  95
Asp Gly Asp Phe Ala Ile Val His Met Thr Lys Leu Leu Leu Asp Tyr
                100                 105                 110
Thr Gly Lys Ile Met Trp Thr Pro Pro Ala Ile Phe Lys Ser Tyr Cys
        115                 120                 125
Glu Ile Ile Val Thr His Phe Pro Phe Asp Gln Gln Asn Cys Thr Met
    130                 135                 140
Lys Leu Gly Ile Trp Thr Tyr Asp Gly Thr Lys Val Ser Ile Ser Pro
145                 150                 155                 160
Glu Ser Asp Arg Pro Asp Leu Ser Thr Phe Met Glu Ser Gly Glu Trp
                165                 170                 175
Val Met Lys Asp Tyr Arg Gly Trp Lys His Trp Val Tyr Tyr Thr Cys
            180                 185                 190
Cys Pro Asp Thr Pro Tyr Leu Asp Ile Thr Tyr His Phe Ile Met Gln
        195                 200                 205
Arg Ile Pro Leu Tyr Phe Val Val Asn Val Ile Ile Pro Cys Leu Leu
    210                 215                 220
Phe Ser Phe Leu Thr Gly Leu Val Phe Tyr Leu Pro Thr Asp Ser Gly
225                 230                 235                 240
Glu Lys Met Thr Leu Ser Ile Ser Val Leu Leu Ser Leu Thr Val Phe
                245                 250                 255
Leu Leu Val Ile Val Glu Leu Ile Pro Ser Thr Ser Ser Ala Val Pro
                260                 265                 270
```

―continued

```
Leu Ile Gly Lys Tyr Met Leu Phe Thr Met Ile Phe Val Ile Ser Ser
        275                 280                 285

Ile Ile Ile Thr Val Val Ile Asn Thr His His Arg Ser Pro Ser
        290             295             300

Thr His Thr Met Pro Gln Trp Val Arg Lys Ile Phe Ile Asp Thr Ile
305             310             315                 320

Pro Asn Val Met Phe Phe Ser Thr Met Lys Arg Ala Ser Lys Glu Lys
                325             330             335

Gln Glu Asn Lys Ile Phe Ala Asp Asp Ile Asp Ile Ser Asp Ile Ser
            340             345             350

Gly Lys Gln Val Thr Gly Glu Val Ile Phe Gln Thr Pro Leu Ile Lys
        355             360             365

Asn Pro Asp Val Lys Ser Ala Ile Glu Gly Val Lys Tyr Ile Ala Glu
    370             375             380

His Met Lys Ser Asp Glu Glu Ser Ser Asn Ala Ala Glu Glu Trp Lys
385             390             395             400

Tyr Val Ala Met Val Ile Asp His Ile Leu Leu Cys Val Phe Met Leu
            405             410             415

Ile Cys Ile Ile Gly Thr Val Ser Val Phe Ala Gly Arg Leu Ile Glu
            420             425             430

Leu Ser Gln Glu Gly
        435
```

METHODS TO TREAT UNDESIRABLE IMMUNE RESPONSES

CROSS-REFERENCE TO RELATED APPLICATION

This application is a continuation-in-part of U.S. patent application Ser. No. 08/564,972, filed Nov. 30, 1995 which is incorporated by reference herein.

STATEMENT OF GOVERNMENT RIGHTS

The present invention was made with the support of the United States Government (National Institute of Neurological and Communicative Disorders and Strokes, Grant NS 23919). The Government may have certain rights in the invention.

BACKGROUND OF THE INVENTION

Ideal treatments for a pathological condition or disease caused by an undesirable immune response would specifically affect antigen-specific T and B cells. Antigen specific tolerization of T cells can be obtained by delivery of the antigen through routes, such as oral, intraperitoneal and nasal administration, that downregulate, rather than activate, CD4+ responses (Matzinger, 1994; Nossal, 1995). Tolerization of T cells by those routes has proven effective for the prevention and/or treatment of CD4+ T cell mediated autoimmune diseases, e.g., experimental autoimmune encephalomyelitis (EAE) (Metzler et al., 1993; Miller et al., 1994; Genain et al., 1996; Al-Sabbagh et al., 1996), collagen-induced arthritis (Al-Sabbagh et al., 1996), and experimental uveitis (Dick et al., 1993). Moreover, the administration of the antigen by these methods reduced or inhibited the immune response specific for the particular antigen administered. For example, aerosol administration of myelin basic protein (MBP) to MBP-immunized rats that had developed relapsing EAE decreased the intensity of the immune response to MBP and the severity of the attacks (Al-Sabbagh et al., 1996). Spleen T cells from rats that had inhaled MBP transferred protection to naive animals (Al-Sabbagh et al., 1996).

It is unclear whether similar approaches could be used for antibody (Ab)-mediated diseases for two reasons. First, while effective at reducing antigen-specific CD4+ responses, administration of antigen through routes that downregulate CD4+ responses may directly stimulate B cells specific for the administered antigen (Kuper et al., 1992; Liu et al., 1993; Husby et al., 1994; Neutra et al., 1996). This stimulation may have disastrous consequences, as has been shown in marmoset EAE (Genain et al., 1996), where intraperitoneal administration of myelin resulted in CD4+ tolerance to myelin, but also in an acute, fatal form of EAE. The fatal form of EAE was characterized by antibody specific for the myelin oligodendrocyte glycoprotein. Second, administration of antigen through routes that stimulate Th2 cells and downregulate pro-inflammatory Th1 cells can stimulate antibody synthesis (Neutra et al., 1996; Abbas et al., 1996), and cause exacerbation rather than improvement of antibody-mediated autoimmune diseases.

Short T epitope sequences may be safer for inducing T cell tolerance than the whole antigen molecule, since peptide-specific antibodies very seldom crossreact with the cognate native antigen (Conti-Fine et al., 1996). Peptides have been used with dubious success for oral tolerization in EAE (Karpus et al., 1996; Metzler et al., 1993), although peptides are not ideal for oral tolerization because they are easily digested by gastrointestinal proteases.

Thus, there is a need for an improved method to treat or inhibit antibody-mediated diseases.

SUMMARY OF THE INVENTION

The present invention provides a therapeutic method comprising the administration of an "epitope" peptide comprising a universal and/or immunodominant epitope sequence derived from a particular antigen that is associated with an antibody-mediated disease in a mammal. The method is effective to specifically tolerize, or down regulate the priming and/or activity of, the antigen-specific T cells of said mammal. The sequence of the epitope peptide does not include the entire sequence of the antigen from which it is derived.

Many autoimmune diseases and other pathological conditions are directly caused by antibodies. Such antibodies are directed against proteins or other antigenic components of the host in diseases such as autoimmune diseases, or against exogenous substances in, for example, allergic diseases. The antibodies may also be directed against therapeutic agents, i.e., proteins or other antigenic substances given to the host for therapeutic purposes, such as the administration of factor VIII to treat bleeding in hemophilia A patients. These therapeutic agents may be administered exogenously, or may be synthesized by the host as a result of gene therapy.

Antibody synthesis is controlled by T cells. In mammals there are limited sets of epitopes for each antigen that dominate the T cell response, referred to as immunodominant T cell epitope sequences (hereinafter "immunodominant epitope sequences"). Moreover, in humans, CD4+ cells recognize universal, immunodominant epitope sequences. As T cell epitopes may comprise as few as 7 amino acid residues corresponding to an amino acid sequence present in a particular antigen, peptides having at least about 7 amino acid residues may be useful to tolerize, or down regulate the priming and/or activity of, T cells (e.g., CD4+ cells) specific for the peptide and its corresponding antigen. Thus, immunodominant and/or universal epitope peptides may be administered so as to regulate a mammal's T cell and antibody response.

To determine whether the delivery of a given peptide is useful to inhibit or treat a particular indication or disease in humans, the immunodominant and/or universal epitopes for a relevant antigen are identified. These epitopes are then identified, synthesized and administered to non-human mammals, preferably ones that are models for a particular human indication or disease, to determine whether the epitope peptide is useful to down regulate the T cell and antibody response to a particular antigen. For example, rodents immunized with Torpedo fish AChR (TAChR) and, thus, susceptible to experimental myasthenia gravis (EMG) are useful to determine whether the administration of acetylcholine receptor (AChR)-derived epitope peptides can result in T cell tolerization. As described hereinbelow, EMG was induced in C57B1/6 (B6) mice by immunization with purified TAChR. The immunized animals have sensitized CD4+ and B cells, and produce high affinity IgG antibodies which cross-react with mouse muscle AChR. The immunized B6 mice have anti-TAChR CD4+ T cells that recognize primarily epitopes within residues 146–169, 181–200 and 360–378 of the TAChR a subunit. Surprisingly, nasal administration of synthetic sequences of the TAChR a subunit representing epitopes recognized by anti-TAChR CD4+ T helper cells, given before and during immunization with TAChR, resulted in 1) decreased CD4+ responsiveness to those epitopes and to TAChR; 2) reduced synthesis of anti-TAChR antibodies; and 3) an absence of EMG.

Likewise, hemophilia A mice (factor VIII knockout mice), which do not produce factor VIII but produce anti-factor VIII antibodies after exogenous administration of factor VIII, are useful to test whether factor VIII T cell epitope peptides can down regulate the anti-factor VIII immune response in these mice.

With respect to universal, immunodominant CD4+ epitopes in humans, it has been shown that diphtheria toxin (DTX) and tetanus toxin (TTX) have such epitopes, see U.S. application Ser. No. 08/564,972; Raju et al., 1995; Raju et al.,1996; Diethelem et al., 1997), respectively. As described hereinbelow, universal, immunodominant CD4+ epitope sequences exist on human AChR, the endogenous protein that is associated with the sensitization of CD4+ cells and production of high affinity IgG in myasthenia gravis (MG) patients. Moreover, the universal, immunodominant epitope sequences recognized by CD4+ T cells of MG patients can lead to the synthesis of pathogenic anti-AChR antibodies (Conti-Fine et al., 1997). Also as described hereinbelow, the majority of humans sensitized to factor VIII have CD4+ cells that recognize certain universal epitopes of factor VIII.

In particular, respiratory, e.g., nasal (upper) or lower respiratory tract, administration is a promising tolerizing route when using an epitope peptide, since the peptide does not need to overcome the proteolytic barriers present in the digestive system, and crosses the epithelia more readily than larger polypeptide molecules. Thus, synthetic CD4+ epitope sequences may be more effective than the whole or native antigen for tolerance induction. Moreover, the peptides of the invention can be prepared in large quantities and in high purity by chemical syntheses and thus are much less expensive and more readily obtained than a preparation comprising isolated autoantigen. Further, the delivery of epitope peptides to other mucosal surfaces, e.g., in the intestine, the mouth, the genital tract, and the eye, may also be employed in the practice of the methods of the invention, although the invention is not limited to administration by mucosal routes.

The administration of peptides to mucosal surfaces can result in a state of peripheral tolerance, a situation characterized by the fact that immune responses in non-mucosal tissues do not develop even if the peptide initially contacted with the mucosa is reintroduced, or its corresponding antigen is introduced or interacts with the immune system (e.g., in autoimmune diseases), in the organism by a non-mucosal route. Since this phenomenon is exquisitely specific for the peptide, and thus does not influence the development of systemic immune responses against other antigens, its use is particular envisioned for preventing and treating illnesses associated or resulting from the development of exaggerated immunological reactions against specific antigens encountered in nonmucosal tissues. For example, one embodiment of the invention is a method in which a mammal is contacted with a peptide of the invention via nasal inhalation in an amount that results in the T cells of said mammal having diminished capability to develop a systemic and/or peripheral immune response when they are subsequently contacted with an antigen comprising an immunodominant and/or universal portion of said peptide.

Thus, the invention provides a method of preventing or inhibiting an indication or disease associated with aberrant, e.g., excessive, pathogenic or otherwise undesirable antibody production. The method comprises administering to a mammal afflicted with, or at risk of, the indication or disease an amount of a peptide, a variant thereof or a combination thereof, that is formally a fragment of a native antigen, and having an immunodominant and/or universal epitope sequence of said antigen which is effective to prevent or inhibit at least one symptom of the indication or disease. Preferably, for humans, the peptide comprises a universal, immunodominant epitope sequence. It is preferred that the peptide is administered to a mucosal surface. A preferred mucosal surface to which the peptides of the invention are administered is the respiratory tract.

Also provided is a method in which the administration of a peptide of the invention to a mammal results in the suppression, tolerization, or down regulation of the priming and/or activity, of T cells of a mammal at risk or, or having, an indication or disease associated with aberrant, pathogenic or otherwise undesirable antibody production. Further provided is a method in which the administration of a peptide of the invention results in the decrease in the amount or activity of antibodies which are characteristic of the particular disease or indication. Preferably, the administration of a peptide of the invention to a mammal results in T cell tolerization, the down regulation of priming or activity of T cells, a reduction in the amount or affinity of pathogenic antibodies, the inhibition of at least one symptom of the indication or disease, or any combination thereof.

The invention also provides a method to prevent or inhibit an indication or disease characterized by the presence of an antibody specific for an endogenous antigen. The method comprises administering to a mammal in need thereof an effective amount of a peptide, a variant thereof, or a combination thereof, wherein the peptide represents a fragment of said antigen and comprises an immunodominant and/or universal epitope sequence of said antigen. The administration is effective to reduce or eliminate at least one symptom of the indication or disease, tolerize or down regulate the priming or activity of T cells specific for the epitope and the antigen comprising said epitope, and/or decrease the amount or affinity of the antibody for the endogenous antigen. Indications and diseases characterized by the presence of an antibody which binds an endogenous antigen include antibody-mediated autoimmune diseases such as myasthenia gravis, systemic lupus erythematosus, pemphigus, thrombic thrombocytopenic purpura and the like.

Preferably, the peptide is nasally administered to a human in an amount effective to suppress or tolerize, or down regulate the priming or activity of, the CD4+ cells of said human which induce the production of pathogenic antibodies. A preferred peptide to prevent or treat myasthenia gravis is a peptide that comprises a universal and/or immunodominant epitope sequence of human AChR. Likewise, preferred peptides that are useful to prevent or treat the undesirable immune responses to factor VIII that may develop in hemophilia A patients after treatment with factor VIII, or to factor IX that may develop in hemophilia B patients after treatment with factor IX, would be universal and/or immunodominant CD4+ epitope sequences of factor VIII and factor IX, respectively.

Yet another embodiment of the invention is a method to prevent or inhibit an indication or disease characterized by the presence of an antibody specific for an exogenous antigen, wherein the antigen is not associated with an infectious agent, e.g., a virus, bacteria or fungus, with the exception of viruses employed to transfer genes for gene therapy, and fungal components that cause allergic responses. The method comprises administering to a mammal in need thereof an amount of a peptide, a variant thereof, or a combination thereof, effective to reduce or eliminate at least one symptom of the indication or disease, tolerize or down regulate the priming or activity of, T cells specific for the epitope and/or decrease the amount or affinity of the antibody specific for the exogenous antigen. The administered peptide is a fragment of said antigen and comprises an immunodominant and/or universal epitope sequence of the exogenous antigen. For example, allergies are characterized by an exaggerated immune response to certain environmental factors. Thus, to prevent or inhibit an exaggerated antibody-mediated immune response to a proteinaceous allergen, an effective amount of a peptide comprising an immunodominant and/or universal epitope sequence of the allergen, is administered to the mammal.

Further provided is a method to tolerize a mammal to an antigen associated with aberrant or pathogenic, or otherwise undesirable, antibody production in the mammal. The method comprises administering to the mammal an amount of at least one peptide, a variant thereof or a combination thereof, having a universal and/or immunodominant epitope sequence effective to tolerize, or down regulate the priming or activity of T cells of, the mammal to an antigen comprising said epitope, wherein said peptide is a fragment or subunit of said antigen.

Yet another embodiment of the invention is a method to identify an immunodominant epitope sequence in a mammal. The method comprises contacting at plurality of samples with a panel of peptides. Each sample comprises T cells and antigen presenting cells obtained from an individual mammal. The panel of peptides together correspond to the entire sequence of a particular antigen. Preferably, the peptides comprise overlapping sequences, i.e., each peptide comprises a sequence which overlaps with a portion of the sequence of at least one other peptide, such as the two adjacent peptides. Each sample is contacted with one of the peptides. Preferably, the mammals have been previously exposed to the antigen. Then it is determined whether the T cells from the mammal proliferate in response to one of the peptides relative to a sample contacted with an unrelated peptide that does not comprise an immunodominant epitope sequence and/or a sample which is not contacted with a peptide.

Another embodiment of the invention is a method to identify a universal epitope sequence useful to tolerize, or down regulate the priming or activity of, T cells of a mammal, e.g., a human. The method comprises contacting at least two samples with a preselected peptide, a variant thereof or combination thereof. One sample comprises T cells obtained from a first individual mammal. The second sample comprises T cells from a second mammal, wherein the genotype of the second mammal differs at the immune response loci from the genotype of the first mammal, and wherein the mammals are of the same species. The samples to be tested preferably comprise T cells of a mammal that are sensitized to an antigen comprising said peptide. Preferably, the T cells are obtained from a mammal having, or at risk of, an indication or disease associated with aberrant or pathogenic, or otherwise undesirable, antibodies to the antigen. Then it is determined whether or not the T cells from each mammal proliferate relative to (negative) control T cells which were not exposed to a peptide or any other antigenic stimulus, and/or relative to T cells exposed to a (negative) control peptide, i.e., one not having a universal epitope sequence. A peptide having a universal epitope sequence will induce the proliferation of T cells from samples from a majority of mammals of the same species, mammals which differ at the immune response loci.

Thus, the invention also provides a tolerogen comprising at least one isolated and purified epitope peptide having a universal and/or immunodominant epitope sequence and a physiologically compatible carrier, the administration of which to a sensitized mammal results in the suppression or reduction of the immune response of that mammal to an antigen which comprises at least an immunogenic portion of the peptide. Alternatively, the administration of at least one isolated and purified epitope peptide having a universal and/or immunodominant epitope sequence and a physiologically compatible carrier, to a non-sensitized mammal results in the blocking of or a reduction in the priming to an antigen which comprises at least an immunogenic portion of the peptide, when such antigen is administered to the mammal in a manner that normally results in an immune response. It is preferred that the peptide contains a contiguous sequence of at least about 7 amino acids having identity with the amino acid sequence of the antigen, and that the peptide is no more than about 40 amino acid residues in length, i.e., it represents a subunit of said antigen. It is also preferred that the tolerogen is nasally administered.

A further embodiment of the invention is a method to inhibit or suppress an antibody-mediated disease that is associated with the administration of an endogenous protein or the use of gene therapy to replace such a protein. An endogenous protein that is administered so as to supplement or replace a deficiency in that protein includes, but is not limited to, insulin or fragments thereof, gamma globulins or fragments thereof, factor VIII or fragments thereof, factor IX or fragments thereof, cystic fibrosis transmembrane regulator or fragments thereof, growth hormone or fragments thereof, a transplantation antigen or fragments thereof and the like. Moreover, the endogenous protein may be recombinantly produced (referred to as "recombinant" protein or polypeptide). Replacement gene therapy includes the use of viral vectors to introduce and express a therapeutic gene, e.g., an endogenous protein. Because the endogenous protein or exogenous viral protein is "foreign" to the host, the host may have an immune response to these proteins. To suppress this response, a mammal at risk of, or having, a disease characterized by a decreased amount of, or a lack of, an endogenous protein or polypeptide, e.g., hemophilia A or B, adenosine deamidase deficiency, cystic fibrosis or diabetes, is administered a peptide, a variant thereof or a combination thereof in an amount effective to suppress or tolerize, or down regulate the priming and/or activity of, T cells specific for the endogenous protein. Similarly, to suppress an immune response to a viral protein present in a delivery vehicle for gene therapy, a mammal in need of gene therapy or subjected to gene therapy is administered a peptide, a variant thereof or a combination thereof in an amount effective to suppress or tolerize, or down regulate the priming and/or activity of, T cells specific for the viral protein. Preferably, the epitope peptide is a subunit of the endogenous protein and comprises inmnunodominant and/or universal epitope sequences derived from the endogenous protein, e.g., peptides of factor VIII for hemophilia A, or an epitope peptide derived from the viral protein of the viral vector employed for gene therapy, e.g., peptides of a retrovirus or adenovirus glycoprotein or capsid protein.

Also provided is a therapeutic method, comprising: nasally administering to a mammal subjected to gene therapy which employs a recombinant virus as a delivery vehicle, an amount of an epitope peptide, a variant thereof or a combination thereof effective to suppress an immune response to the virus-specific proteins present in the delivery vehicle, wherein the peptide comprises an immunodominant and/or universal epitope sequence of the virus protein.

Further provided is therapeutic method, comprising: nasally administering to a mammal having an indication or disease characterized by a decreased amount or a lack of an endogenous protein, wherein the mammal is subjected to exogenous introduction of the protein or the corresponding recombinant polypeptide, an amount of an epitope peptide, a variant thereof or a combination thereof effective to suppress an immune response to the exogenously introduced protein or polypeptide, wherein the indication or disease is associated with aberrant or pathogenic antibody production to the endogenous protein, and wherein the epitope peptide is a subunit of the endogenous protein and comprises an immunodominant and/or universal epitope sequence of the endogenous protein.

Also provided is a method to treat an antibody-mediated disease in a mammal wherein the disease is characterized by antibodies specific for an antigen. The method comprises administering to the mammal a dosage form comprising an amount of at least one epitope peptide, a variant thereof or a combination thereof, effective to prevent or inhibit at least one symptom of said disease, suppress or tolerize, or down regulate the priming and/or activity of, T cells specific for the antigen, and/or inhibit or decrease the amount or activity of the antibody which is specific for the antigen. The peptide is a fragment of the antigen and comprises an immunodominant and/or universal epitope sequence of the antigen comprises the immunodominant and/or universal epitope sequence. The mammal is also subjected to plasmapheresis either before, during or after, or any combination thereof, peptide administration so as to decrease the amount of circulating antibodies which include the antibodies specific for the antigen. Optionally, an immunosuppressive agent may also be administered so as to decrease B cell activation.

BRIEF DESCRIPTION OF THE FIGURES

FIG. 5. Nasal administration of synthetic DTX peptides does not affect the development of EMG or the anti-AChR T cell response.

FIG. 9. Codons for specified amino acids.

FIG. 10. Exemplary and preferred amino acid substitutions for variant peptides or polypeptides of the invention.

DETAILED DESCRIPTION OF THE INVENTION

Definitions

Figure 1A:
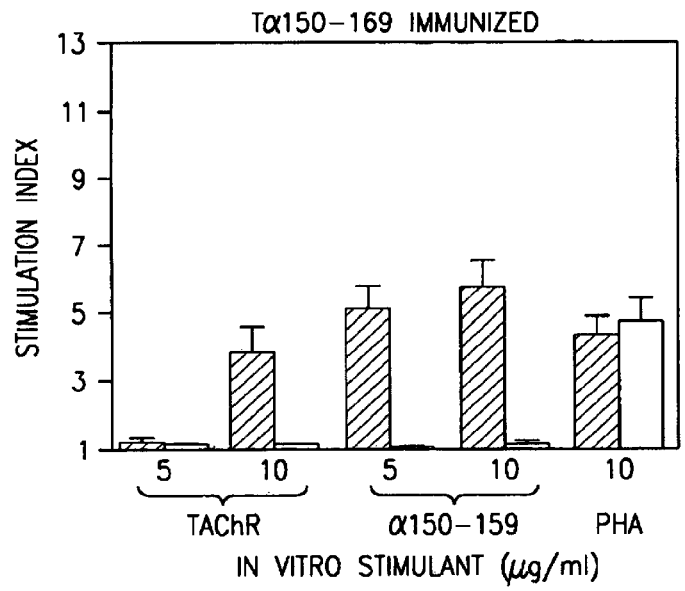
FIGS. 1A–B. Nasal administration of synthetic TAChR epitopes Tα150–169, Tα181–200 and Tα360–378 causes T cell unresponsiveness to those epitopes. Mice were given two nasal administrations of peptide Tα150–169 (FIG. A, white columns), or α pool (FIG. 1B, white columns), or peptide-free PBS (hatched columns) prior to immunization with the peptide(s) used for the nasal treatment. Seven-ten days after the last immunization, the proliferative response of spleen T cells to the immunizing peptide(s) and to TAChR was tested. The data depicted are the results obtained for one mouse from each group, which is representative of the results obtained for all mice of that group. The response induced by 10 µg of PHA is also shown. The columns represent the average S.I. of triplicate cultures. The average c.p.m. obtained in the absence of any stimulation were 297±59 in experiment A and 2,884±106 in experiment B.

"Immunodominant" CD4+ cell epitopes (also referred to as immunodominant T cell epitopes or immunodominant epitope sequences) refer to a sequence of a protein antigen, or the proteinaceous portion of an antigen, that is strongly recognized by the CD4+ cells of a mammal sensitized to that antigen, as detected by methods well known to the art, including methods described herein. "Strongly" recognized means that (he peptide elicits a statistically significant response as compared to the background response to a non-related peptide from an antigen to which the mammal is not sensitized, and that such response is at least two times higher than the average response obtained for at least about ⅓ of the peptides which elicit the lowest response from the peptides employed to identify the immunodominant epitopes.

T cell epitopes can vary in size, and as few as 7 consecutive amino acid residues of a particular antigen may be recognized by CD4+ cells. Thus, an immunodominant epitope sequence is an amino acid sequence containing the smallest number of contiguous amino acid residues which are strongly recognized by T cells from an individual mammal. An epitope peptide of the invention may comprise more than one immunodominant epitope sequence, and may comprise sequences which do not contain an immunodominant epitope sequence. Sequences which do not contribute to an immunodominant epitope sequence can be present at either or both the amino- or carboxyl-terminal end of the peptide. The non-immunodominant epitope sequences preferably are no more than about 10–20 peptidyl residues in toto, and either do not affect the biological activity of the peptide or do not reduce the activity of the peptide by more than 10–20%. Preferably, epitope peptides having immunodominant epitope sequences are useful to tolerize, or down regulate the priming and/or activity of T cells of, a mammal to an antigen having said sequences so as to result in a reduction in the amount or activity of antibodies to said antigen in said mammal.

As used herein, a "universal" epitope sequence is an epitope that is recognized by CD4+ cells from a majority, preferably at least about 66%, more preferably at least about 75%, of individuals within a population of a particular mammalian species that is genetically divergent at the immune response loci, e.g., at the HLA loci in humans. T cell epitopes can vary in size, and as few as 7 consecutive amino acid residues of a particular antigen may be recognized by CD4+ cells. Thus, within the scope of the invention, a universal epitope comprises an amino acid sequence containing the smallest number of contiguous amino acid residues which are recognized by CD4+ cells from a majority of mammals from the same species which are genetically different at their immune response loci. A peptide of the invention may comprise more than one universal epitope sequence, and may comprise sequences which do not contain a universal epitope sequence. Preferably, at least a majority, i.e., 51%, of the amino acid sequence of the peptide comprises a universal epitope sequence. Sequences which do not contribute to a universal epitope sequence can be present at either or both the amino- or carboxyl-terminal end of the peptide. The non-universal epitope sequences preferably are no more than about 10–20 peptidyl residues in toto, and either do not affect the biological activity of the peptide or do not reduce the activity of the peptide by more than 10–20%.

The term "tolerance" is here defined as a reduction in the T cell and/or antibody response which is specific for a given antigen. The reduction in the antibody response may be concomitant with increased sensitization and/or response of special subsets of T cells specific for the antigen, for example CD4+ Th2 cells which have immunoregulatory functions.

As used herein, the terms "isolated and/or purified" refer to in vitro preparation, isolation and/or purification of a peptide or nucleic acid molecule of the invention, so that it is not associated with in vivo substances, or is substantially purified from in vitro substances.

As used herein, the term "immunogenic" with respect to a peptide of the invention means that the peptide can induce non-tolerized peripheral blood mononuclear cells (PBMC) or other lymphoid cells from a sensitized mammal to proliferate or secrete cytokines when those cells are exposed to the peptide relative to cells not exposed to the peptide, and/or that the administration of the peptide to a mammal causes an immune response to the peptide.

A "sensitized" mammal is a mammal that has been exposed to a particular antigen, as evidenced by the presence of antibodies or T cells specific to the antigen. Preferably, the mammal has high affinity, e.g., IgG, antibodies to the antigen. A sensitized mammal within the scope of the invention includes mammals having or at risk of an antibody-mediated indication or disease as defined herein.

As used herein, an "exogenous" antigen does not include antigens of an infectious agent, e.g., a virus, bacteria or fungus, with the exception of viruses employed to transfer genes for gene therapy, and fungal components that cause allergic responses.

As used herein, an "endogenous" antigen includes proteins that are normally encoded by the genome of and expressed in a mammal.

As used herein, the term "aerosol" includes finely divided solid or liquid particles that may be created using a pressurized system such as a nebulizer or instilled into a host. The liquid or solid source material contains a peptide or a nucleic acid molecule of the invention, or a combination thereof.

An "epitope" peptide of the invention is a peptide subunit that comprises at least about 7 and no more than 40 amino acid residues which have 100% contiguous amino acid sequence homology or identity to the amino acid sequence of a particular antigen, e.g., human AChR or factor VIII. An epitope peptide of the invention comprises a universal and/or immunodominant epitope sequence. The administration of an epitope peptide of the invention to a sensitized mammal results in a mammal that is tolerized to the antigen from which the epitope peptide is derived. Preferably, the administration of an epitope peptide of the invention to a mammal does not result in the stimulation of B cells specific for the peptide.

As employed herein, a "variant" of an epitope peptide of the invention refers to a peptide which comprises at least about 7 and no more than about 40, peptidyl residues which have at least about 70%, preferably about 80%, and more preferably about 90%, but less than 100%, contiguous homology or identity to the amino acid sequence of a particular antigen. A variant peptide of the invention comprises a universal and/or immunodominant epitope sequence. The administration of a variant peptide of the invention to a sensitized mammal results in a mammal that is tolerized to the peptide, and to the antigen from which the peptide is derived. Preferred variant peptides of the invention do not reduce the biological activity of the peptide by more than 10–20% relative to the corresponding non-variant peptide.

As used herein, the term "biological activity" with respect to a peptide of the invention is defined to mean that the administration of the peptide, preferably via a mucosal surface such as the respiratory tract, to a mammal results in the mammal developing tolerance to an antigen having at least a portion of the peptide administered.

"Replacement gene therapy" as used herein means therapy intended to supplement reduced amounts or the complete absence of an endogenous protein. The therapy may include the administration of isolated native protein or recombinant polypeptide to the mammal in need thereof, or the administration of a recombinant viral vector encoding said polypeptide.

An "indication or disease" within the scope of the invention includes antibody-mediated diseases as well as cell-mediated diseases. Antibody-mediated diseases include, but are not limited to, autoimmune diseases such as myasthenia gravis, and allergic diseases such as those described below. Antibody-mediated indications within the scope of the invention include, but are not limited to, indications characterized by undesirable antibody responses to substances administered for therapeutic purposes such as antibody responses to endogenous proteins that are exogenously administered, and to viral proteins or the protein encoded by a viral vector that is employed for gene therapy.

I. The Immune Response

The capacity to respond to immunologic stimuli resides primarily in the cells of the lymphoid system. During embryonic life, a stem cell develops, which differentiates along several different lines. For example, the stem cell may turn into a lymphoid stem cell which may differentiate to form at least two distinct lymphoid populations. One population, called T lymphocytes, is the effector agent in cell-mediated immunity, while the other, called B lymphocytes, is the primary effector of antibody-mediated, or humoral, immunity. The stimulus for B cell antibody production is the attachment of an antigen to B cell surface immunoglobulin. Thus, B cell populations are largely responsible for specific antibody production in the host. For most antigens, B cells require the cooperation of antigen-specific T helper (CD4+) cells for effective production of high affinity antibodies.

Of the classes of T lymphocytes, T helper (Th) or CD4+ cells, are antigen-specific cells that are involved in primary immune recognition and host defense reactions against bacterial, viral, fungi and other antigens. CD4+ cells are necessary to trigger high affinity IgG production from B cells for the vast majority of antigens. The T cytotoxic (Tc) cells are antigen-specific effector cells which can kill target cells following their infection by pathologic agents.

While CD4+ cells are antigen-specific, they cannot recognize free antigen. For recognition and subsequent CD4+ activation and proliferation to occur, the antigen must be processed by suitable cells (antigen presenting cells, APC). APC fragment the antigen molecule and associate the fragments with major histocompatibility complex (MHC) class II products (in humans) present on the APC cell surface. These antigen fragments, or T cell epitopes, are thus presented to receptors or a receptor complex on the CD4+ cell in association with MHC class II products. Thus, CD4+ cell recognition of a pathogenic antigen is MHC class II restricted in that a given population of CD4+ cells must be either autologous or share one or more MHC class II products with the APC. Likewise, Tc cells recognize antigen in association with MHC class I products.

In the case of CD4+ cells, this antigen presenting function is performed by a limited number of APC. It is now well established that CD4+ cells recognize peptides derived from processed soluble antigen in association with class II MHC product, expressed on the surface of macrophages. Recently, other cell types such as resting and activated B cells, dendritic cells, epidermal Langerhans' cells, and human dermal fibroblasts have also been shown to present antigen to CD4+ T cells.

If a given CD4+ cell possesses receptors or a receptor complex which enable it to recognize a given MHC class II product-antigen complex, it becomes activated, proliferates and generates lymphokines, such as interleukin 2 (IL-2). The lymphokines in turn cause the proliferation of several types of "killer" cells, including Tc cells and macrophages, which can exhibit antimicrobial and tumoricidal activity.

After stimulation subsides, survivors of the expanded CD4+ cells remain as member cells in the body, and can expand rapidly again when the same antigen is presented.

Numerous attempts have been made to isolate and maintain homogenous populations of Tc or CD4+ cells and to characterize them in terms of their antigen specificity and MHC restriction. These attempts usually involve the stimulation of mononuclear cells from a seropositive human or murine host with antigenic bacterial or viral preparations in combination with nonproliferative APC, such as irradiated autologous mononuclear cells (MNC). Proliferating polyclonal populations of CD4+ cells or Tc cells can be cloned by limiting dilution to obtain homogenous populations and then further proliferated and characterized by a variety of techniques.

Methods of determining whether PBMCs or lymphoid cells have proliferated, or produced or secreted interleukins, are well known in the art. For example, see Paul, *Fundamental Immunology*, 3rd ed., Raven Press (1993), and Benjamini et al. (eds.), *Immunology: A Short Course*, John Wiley & Sons, Inc., 3rd ed. (1996).

II. Indications Amenable to Treatment by the Peptides of the Invention, or Nucleic Acid Molecules Encoding the Peptides The peptides or nucleic acid molecules of the invention are useful to treat a mammal afflicted with, or to inhibit in a mammal at risk of, an indication or a disease characterized by aberrant or pathological, or undesirable, antibody production which is specific for a particular antigen, e.g., an antibody-mediated autoimmune disease. Preferably, these efficacious peptides are recognized by CD4+ cells from a majority of mammals having or at risk of the indication or disease, and, more preferably, these epitopes are recognized by CD4+ cells that induce the synthesis of pathogenic antibody and/or excessive amounts of the antibody. Indications or diseases associated with aberrant, pathological or undesirable antibody production include, but are not limited to, autoimmune disease (endogenous antigen), replacement gene therapy (endogenous and/or exogenous antigen), proteins administered for therapeutic purposes (endogenous and/or exogenous antigen) or allergies (exogenous antigen). Thus, a peptide may be selected so as to inhibit or treat an indication or disease characterized by aberrant, pathological or undesirable antibody production which is antigen specific, thereby minimizing side effects resulting from disrupting unrelated physiological processes or side effects associated with administration of full-length antigen.

A. Autoimmune Diseases

Autoimmune diseases are characterized by an abnormal immune response involving either cells or antibodies, that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimmune diseases include multiple sclerosis, rheumatoid arthritis, Hashimoto thyroiditis, type I diabetes mellitus (Juvenile onset diabetes) and autoimmune uvoretinitis (see Table 1). Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia (see Table 1). The antigen(s) associated with systemic lupus erythematosus is small nuclear ribonucleic acid proteins (Snurps), Graves' disease is the thyrotropin receptor, thyroglobulin and other components of thyroid epithelial cells (Akamizu et al., 1996; Kellerman et al., 1995; Raju et al., 1997; and Texier et al., 1992), pemphigus is cadherin-like pemphigus antigens such as desmoglein 3 and other adhesion molecules (Memar et al., 1996: Stanley, 1995; Plott et al., 1994; and Hashimoto, 1993), and thrombic thrombocytopenic purpura is antigens of platelets.

Other autoimmune diseases and their specific autoantigens and/or target tissues are disclosed in Schwartz, R. S. et al. in *Fundamental Immunology*, Third Edition, Paul, W. E., Ed., Raven Press, New York, 1993, which is incorporated by reference herein.

The current treatments for both categories of autoimmune diseases involve administration of drugs which non-specifically suppress the immune response. Examples of such drugs are methotrexate, cyclophosphamide, Imuran (azathioprine) and cyclosporin A. Steroid compounds such as prednisone and methylprednisolone are also employed in many instances. These drugs have limited efficacy against both cell- and antibody-mediated autoimmune diseases. Use of such drugs is limited by virtue of their toxic side effects and also because they induce "global" immunosuppression in a patient receiving prolonged treatment with the drug, e.g., the normal protective immune response to pathogenic microorganisms is downregulated thereby increasing the risk of infections caused by these pathogens. A further drawback is that there is an increased risk that malignancies developing in patients receiving prolonged global immunosuppression.

TABLE 1

| Disease Model | Specific Autoantigen |
| --- | --- |
| Multiple Sclerosis | MBP |
| Rheumatoid Arthritis | Collagen |
| Autoimmnune Thyroiditis | Thyroglobulin |
| Myasthenia Gravis | Acetylcholine receptor |
| Autoimmune uvoretinitis | S-antigen |
| Systemic Lupus Erythematosus | DNA |
| Diabetes | islet cell extract |
| Chronic Active Hepatitis | Liver extract |
| Adrenalitis | Adrenal gland extract |
| Polymyositis | Muscle extract |
| Autoimmune hemolytic anemia | Hematopoietic cells |
| Rheumatic carditis | Heart extract |
| Scleroderma | Skin cell extract |

An autoimmune disease is a malfunction of the immune system of mammals, including humans. In a mammal afflicted with such a disease, the immune system treats autologous tissues (self or endogenous antigens) and substances as if they were foreign and dangerous, and evokes the immune defense that is usually reserved for use against exogenous and dangerous substances (e.g., foreign tissues or invading organisms), including sensitization of T cells and synthesis of high affinity antibodies.

B. Replacement Therapies which employ Protein Therapeutics or Gene Therapy

The identification of underlying genetic defects has made gene therapy an attractive treatment option for a wide variety of diseases. Gene therapy is particularly useful in indications or diseases that result from a defect in a single gene. A deficiency in an endogenous protein in a mammal may occur neonatally or later in the mammal's life. The deficiency may be a complete lack of the endogenous protein, e.g., due to a genetic defect in the gene encoding the protein, or a reduced amount of an endogenous protein relative to a majority of other mammals of the same species. In either case, the deficiency may be enough to result in a particular disorder or disease. For example, a deficiency in factor VIII causes hemophilia A and a deficiency in factor IX causes hemophilia B. To supplement these deficiencies, certain proteins can be administered to the mammal so as to treat or prevent the disease. A different approach to treat or prevent genetic defects which result in disease is to introduce a "normal" gene that encodes the endogenous protein to the mammal having the deficiency. Viral vectors are one method which has been employed to introduce particular genes into mammals. However, the introduction of endogenous proteins, their recombinantly produced counterpart polypeptides, or recombinant viruses having genomes that encode the endogenous protein can result in an immune response to the foreign proteins, the endogenous protein, the recombinant polypeptide, or the viral capsid or glycoproteins.

Thus, therapies in which an endogenous protein is administered to treat a particular disease can result in an antibody mediated response which is specific for that protein. One example of such a disease is hemophilia. For example, certain hemophiliacs lack or have reduced amounts of factor VIII. These patients are treated with isolated native factor VIII or recombinant factor VIII. However, some of these patients develop antibodies to factor VIII that block of inhibit factor VIII activity that reduces the efficacy and increases the cost of the therapy. Likewise, an immune reaction to a native or recombinant protein that is introduced into a mammal to supplement a deficiency in that protein may be prevented or treated by the compounds, compositions and methods of the invention. Such proteins include, but are not limited to factor IX, growth hormone, adenine deamidase (ADA), β-globin, HPRT, purine nucleoside phosphorylase, α1-anti-trypsin, glucocerebrosidase, argininosuccinate synthase, phenylalanine hydroxylase, low density lipoprotein receptor, interleukins, cytokines, dystrophin, ciliary neurotrophic factor (for ALS), fibrosis transmembrane conductance regulator (for cystic fibrosis), p47, alpha-L-hyaluronidase (Hurler syndrome), prolidase, N-acetylgalactosamine (mucopolysaccharidosis type VI), β-glucuronidase (mucopolysaccharidosis type VIII), ornithine transcarbamylase, liver arginine ureahydrolase, or insulin, may result in the mammal developing antibodies to the administered protein. The methods of the invention are particularly useful to prevent or treat such indications or diseases by tolerizing, or down regulating the priming and/or activity of the T cells of, mammals having such indications or diseases with a peptide having a universal and/or immunodominant epitope sequence from the protein antigen employed for therapeutic purposes.

Successful gene therapy requires the identification of an appropriate therapeutic gene for treatment of the disease, but may also require a delivery system by which that gene can be introduced to the recipient or to a desired cell type both efficiently and accurately. One such delivery system currently employed in clinical trials employs a viral vector to deliver the desired gene to the host organism. The expression of the gene results in the synthesis of the encoded protein in an amount which supplements the amount present in the mammal prior to therapy, preferably so as to inhibit or reduce at least one symptom of the disease.

Viral vectors that have been approved for gene therapy clinical trials include retroviral vectors, adenovirus vectors and adeno-associated virus vectors (see Marshall, *Science*, 269, 1050–1059 (1995)). The introduction of viral vectors and the expression of an endogenous gene product that is not expressed or poorly expressed is that the immune response to the vector-encoded viral proteins (exogenous) results in sensitization of the recipient to those antigens. Thus, the beneficial effects of gene therapy are reduced as a result of the patient's immune system recognizing the viral proteins, as well as the expressed endogenous gene product, as "foreign".

C. Exogenous Antigens

Allergic diseases within the scope of the invention include allergic rhinitis, allergic asthma, atopic dermatitis, allergic gastroentheropathy, anaphylaxis, urticaria and angioedema. Allergens within the scope of the invention include, but are not limited to, protein antigens of *Alternaria altemata* (Alt a I), *Artemisia vulgaris* (Art v II), *Aspergillus fumigatus* (Asp f II), *Dermatophagoides far.* (Der fI), *Dermatophagoides pteron.* (Der p I, Der p III, Der p IV, Der p VI and Der p VIII), and domestic animals such as *Felis domesticus*(Fel d I), cows, pigs, poultry, mice, hamsters, rabbits, rats, guinea pigs, dogs and horses. Common fungal antigens include those of Basidiomycetes such as *Ustilago, Ganoderma, Alternaria, Cladosporium, Aspergillus, Sporobofomyces, Penicillium, Epicoccum, Fusarium, Phoma, Borrytis, Helminthosporium, Stemphylium andCephalosporium*; Phycomycetes such as *Mucor* and *Rhizopus*; and Ascomycetes such as *Eurotium* and *Chaetomium*.

Pollinating plants which may have protein antigens associated with allergies include club mosses, ferns, conifers, flowering plants, grasses, sedges, palms, cattails, nettles, beeches, chenopods, sorrels, willows, poplars, maples, ashes, ragweeds (antigen E, antigen K and Ra3) and sages, or proteinaceous plant products such as those found in latex products.

Hymenoptera insects that may have protein antigens associated with allergies include the honeybee, yellow jacket, homet, wasp and fire ant, although protein antigens of other insects are also within the scope of the invention.

Allergies associated with foods may be the result of protein antigens in crustaceans (e.g., shrimp, lobster and crab), mollusks (e.g., clams), fish, legumes (e.g., peanut, pea, beans, and licorice), seeds (e.g., sesame, cottonseed, caraway, mustard, flaxseed, and sunflower), nuts, berries, egg white, buckwheat and milk.

III. Identification of an Epitope Peptide Falling within the Scope of the Invention The identification of a universal and/or immunodominant epitope sequence in an antigen permits the development and use of a peptide-based tolerogen to the antigen. The administration of epitope peptides which contain a universal and/or immunodominant epitope sequence can induce a tolerizing effect in many, if not all, mammals, preferably those of differing immune response haplotypes. Moreover, the use of peptide tolerogens is less likely to produce the undesirable side effects associated with the use of the full-length antigen. These epitope peptides can be identified by in vitro and in vivo assays, such as the assays described hereinbelow (see, for example, Conti-Fine et al., 1997; and Wang et al., 1997). It is recognized that not all agents falling within the scope of the invention can result in tolerization, or result in the same degree of tolerization.

To identify epitope peptides useful to tolerize a mammal having or at risk of an indication or disease within the scope of the invention, the antigen which is associated with the indication or disease is identified. The antigen may be an endogenous antigen, e.g., the AChR, or an exogenous antigen, e.g., a viral glycoprotein or an endogenous antigen, such as factor VIII, administered exogenously to correct a deficiency in that protein. The amino acid sequence of that antigen is then obtained or determined. Generally, 20 residue peptides are obtained or prepared which span the entire amino acid sequence of the antigen and which overlap the adjacent peptide by 5–10 residues, see U.S. application Ser. No. 08/564,972. In this manner, a peptide may include sequences which correspond to a portion of a universal and/or immunodominant epitope sequence. These peptides are then individually screened in vitro and in vivo.

In vitro methods useful to determine whether a particular peptide comprises a universal and/or immunodominant epitope sequence include determining the biological activity (e.g., inducing the proliferation of or cytokine secretion by T cells) of the peptide in CD4+ cell lines that are specific for an antigen having the peptide, isolated CD4+ cells, CD8+ depleted spleen or lymph node cells, or CD8+ depleted peripheral blood mononuclear cells (PBMC). These cells may be obtained from a mammal at risk or of having an indication or disease within the scope of the invention or from a mammal that is "normal". In either case, the mammal is preferably known to be sensitized to the antigen. Epitope peptides useful in the practice of the invention include a peptide that is strongly recognized by the T cells of the mammal tested, i.e., they have an immunodominant epitope sequence. Preferred epitope peptides are those which are recognized by the T cells of at least a majority of mammals having divergent immune response haplotypes, e.g., MHC class II molecules in humans. This recognition can be measured by the ability of the peptide to induce proliferation or cytokine secretion in T cells obtained from mammals with known or suspected divergent haplotypes and/or by direct HLA class II binding assays (Manfredi et al., 1994; Yuen et al., 1996).

Thus, CD8+ depleted PBMC, CD8+ depleted spleen or lymph node cells or CD4+ lines specific for an antigen or epitope can be contacted with an epitope peptide and the proliferation of the cells measured or the amount and type of cytokine secreted detected. Th1 cytokines include IFN-γ, IL-12 and IL-2. Th2 cytokines include IL-4 and IL-10. An immunospot ELISA or other biological assay is employed to determine the cytokine which is secreted after the peptide is added to the culture.

Epitope peptides falling within the scope of the invention may also be identified by in vivo assays, such as animal models for a particular indication or disease. Generally, the animal is contacted with a particular peptide, or a plurality of peptides, preferably ones which were identified as having immunodominant epitope sequences. The animal is then immunized with an antigen having sequences corresponding to at least a portion, i.e., the immunodominant epitope sequence, of the peptide. The tolerogenic efficacy of the peptide is then determined. For example, T cells may be isolated from these animals and their response to antigen or peptide in vitro measured, or the amount of antibody specific for the antigen obtained at time periods before immunization and after immunization compared. Also, the reduction or inhibition of specific phenotypic indicators of disease, e.g., muscle response in animals having EMG, may be used to determine the tolerogenic effect of the peptide.

One animal model is described in Example I (EMG). Another model is described in Example H. Example II describes how Factor VIII sequences having immunodominant epitope sequences are identified using CD4+ spleen and lymph node cells of hemophilia A mice. Then the identified epitope peptides can be administered to naive hemophilia A mice, preferably by nasal administration, followed by immunization with factor VIII. The efficacy of the tolerizing treatment is then determined by methods similar to those described in Example I.

One example of an antibody-mediated disease for which the cognate antigen is known is MG. Although MG symptoms are due to antibody binding to muscle AChR, circumstantial and direct evidence suggests that CD4+ T helper cells have an important role in the pathogenesis of human MG. The presence of high-affinity anti-AChR IgG antibodies implies that T helper factors lead to a switch to synthesis of antibodies of the IgG isotype by the anti-AChR B cells and to "maturation" of their affinity. Second, anti-AChR reactive CD4+ T cells present in the blood and thymus of MG patients can be propagated in vitro from these tissues, and have T helper function. Third, the only obvious and early effect on the anti-AChR immune response of thymectomy—a staple in the treatment of MG—is an immediate and pronounced decrease in the anti-AChR reactivity of circulating T cells. Fourth, treatment of MG patients with anti-CD4+ antibodies abolishes the T cell response in vitro to the AChR and causes clinical and electrophysiological improvement. Fifth, experiments carried out in a chimeric human-SCID mouse model of passively transferred MG demonstrated that CD4+ cells are indispensable for transfer of the symptoms, and that CD4+ cell lines, derived from MG patients and specific for individual universal epitopes of the α subunit of human AChR can drive the synthesis of pathogenic anti-AChR antibodies that cause MG symptoms.

Several studies have identified sequences of the human AChR α subunit recognized by T cells in MG patients. To determine whether the CD4+ cells recognizing those immunodominant and/or universal epitope sequences can drive the synthesis of pathogenic anti-AChR antibodies, and how the ability of the different sequence regions of the AChR to interact with different HLA DR molecules correlates with the presence of universal CD4+ epitopes, synthetic peptides based on the amino acid sequence of the human α subunit of AChR (Noda et al., *Nature*, 305, 818 (1983); Schoepfer et al., *FEBS Lett.*, 226, 235 (1981)) were prepared. The peptides were approximately 20 residues long, a length that compares with that of naturally processed class H-restricted epitopes, which are 9–14 residues. Extra residues at either end of the epitope sequence do not affect the attachment of the peptide to the binding cleft of the presenting HLA class H molecule, which is open at both its ends. The peptides overlapped by 5–10 residues to reduce the risk of missing epitopes "broken" between peptides.

The response to individual overlapping synthetic AChR peptides spanning the sequence of each AChR subunit, of unselected blood CD4⁻ T cells, and of CD4+ T cell lines enriched with AChR-specific cells by culture in vitro with AChR antigens, was tested. The use of those two cell populations has different advantages and limitations. AChR-specific CD4+ lines have strong, consistent responses to individual peptides that allow a clear-cut assessment of their epitope repertoire. However, they may have an epitope repertoire different from that of the original CD4+ population due to biased clonal propagation in vitro. Also, denatured forms of the antigen such as synthetic and biosynthetic peptides, which are commonly used for propagation of CD4+ cells specific for rare antigens, may be processed into peptide epitopes different from those obtained from processing of the native antigen in vivo and may expand CD4⁻ clones irrelevant for the immune process in vivo. The use of unselected T cells or CD4+ T cells from the blood of MG patients avoids the risk of detecting a biased repertoire due to the selective clonal loss or enrichment, but, because of the low frequency of antigen-specific CD4+ cells, reliable testing of nonselected blood CD4+ T cells is not always successful, especially when assessing the response to individual epitopes.

Due to the "orthogonal" advantages and shortcomings of unselected blood CD4+ cells and of AChR-specific CD4+ lines, it was from the combined results of those two approaches that many AChR sequence regions forming CD4+ epitopes could be confidently identified. The response to the individual AChR peptides of the anti-AChR cell lines was tested by a proliferation assay, and that of unselected blood CD4+ cells by proliferation and enzyme-linked immunospot (ELISPOT) assays. The latter assay type detects the antigen-induced secretion of cytokines (e.g., IFN-γ) by individual CD4+ Th1 cells, demonstrating their role in the anti-AChR CD4+ response. These different approaches have given consistent and complementary results.

The results from these studies, and those of others, which identify sequence regions on each AChR sequence regions on each AChR subunit form CD4+ epitopes are summarized in Table 3. Each patient had an individual repertoire, yet a few sequences on each AChR subunit are recognized by all or most patients, irrespective of the MHC haplotype. The results of studies on the response of blood CD4+ cells indicated that those "universal" epitope sequences are recognized by high numbers of T cells. Thus, they should be considered both universal and immunodominant epitope peptide sequences (indicated by bold characters in Table 3). Their immunodominance may be related to easy cleavage and processing, and to the ability of human DR molecules to interact with many unrelated peptides.

TABLE 3

Sequence Segments of the α, β, γ, δ, and ε Subunits of Human Muscle AChR Forming Epitopes Frequently Recognized by CD4+ Cells in MG Patients α Subunit[a]

| Region α1–80 | Region α101–168 | Region α191–207 | Region α293–337 | Region α387–437 |
|---|---|---|---|---|
| α1–14 | α101–120 | α191–207 | α293–308 | α387–405 |
| α19–34 | α118–137 |  | α304–322 | α403–421 |
| α32–51 | α135–154 |  | α320–337 | α419–437 |
| α48–67 | α151–168 |  |  |  |
| α63–80 |  |  |  |  |

β Subunit[b]

| Region β16–50 | Region β181–200 | Region β271–290 | Region β316–350 | Region β361–425 |
|---|---|---|---|---|
| β16–35 | β181–200 | β271–290 | β316–335 | β361–380 |
| β31–50 |  |  | β331–350 | β376–395 |
|  |  |  |  | β391–410 |
|  |  |  |  | β406–425 |

γ Subunit[c]

| Region γ30–49 | Region γ60–124 | Region γ135–154 | Region γ248–288 | Region γ297–355 | Region γ366–400 | Region γ411–430 | Region γ470–495 |
|---|---|---|---|---|---|---|---|
| γ30–49 | γ60–79 | γ135–154 | γ248–267 | γ297–312 | γ366–385 | γ411–430 | γ470–489 |
|  | γ75–94 |  | γ263–273 | γ306–325 | γ381–400 |  | γ476–495 |
|  | γ90–109 |  | γ269–288 | γ321–340 |  |  |  |
|  | γ105–124 |  |  | γ336–355 |  |  |  |

δ Subunit[d]

| Region δ1–20 | Region δ61–80 | Region δ91–185 | Region δ196–290 | Region δ346–392 | Region δ461–496 |
|---|---|---|---|---|---|
| δ1–20 | δ61–80 | δ91–110 | δ196–215 | δ346–362 | δ461–480 |
|  |  | δ106–125 | δ213–230 | δ363–386 | δ476–496 |
|  |  | δ121–140 | δ226–245 | δ373–392 |  |

TABLE 3-continued

Sequence Segments of the α, β, γ, δ, and ε Subunits of Human Muscle AChR Forming Epitopes Frequently Recognized by CD4+ Cells in MG Patients

|  |  |
|---|---|
| δ136–155 | δ241–260 |
| δ151–170 | δ256–275 |
| δ166–185 | δ271–290 |

ε Subunit

| Region ε51–70 | Region ε91–110 | Region ε121–170 | Region ε231–320 | Region ε351–370 | Region ε431–473 |
|---|---|---|---|---|---|
| ε51–70 | ε91–110 | ε121–140 | ε231–250 | ε351–370 | ε431–450 |
|  |  | ε141–160 | ε241–260 |  | ε451–470 |
|  |  | ε151–170 | ε261–280 |  | ε461–473 |
|  |  |  | ε281–300 |  |  |
|  |  |  | ε291–310 |  |  |
|  |  |  | ε301–320 |  |  |

[a]From Manfredi et al., Neurology, 42, 1092 (1992); Protti et al., Proc. Natl. Acad. Sci. USA, 87, 7792 (1990); and Wang et al., 1997.
[b]From Moiola et al., J. Immunol., 152, 4686 (1994).
[c]From Manfredi et al., J. Clin. Investig., 92, 1055 (1993); and Protti et al., J. Clin. Investig., 90, 1558 (1992).
[d]From Manfredi et al., J. Clin. Investig., 92, 1055 (1993); and Protti et al., J. Immunol., 146, 2253 (1991).

Four AChR α subunit sequences—α48–67, α101–137, α304–322, and the carboxyl-terminal sequence α403–437—are recognized by the majority of the patients, irrespective of their HLA class II type, and by a high number of cells. The peptide sequences recognized by 50% or more of the MG patients are clustered in five sequence regions. One corresponds to residues 1–14; the second corresponds to residues α48–80 and comprises peptides α48–67 and α63–80; the third corresponds to residues α101–154 and includes peptides α101–120, α118–137, and α135–154; the fourth corresponds to residues α304–337 and includes peptides α304–322 and α320–337; and the fifth corresponds to residues α403–437 and includes peptides α403–421 and α419–437. Most of the a subunit sequences recognized by the CD4+ cells correlate with the sequence regions that form non-transmembrane domains, which are believed to be at least partially exposed on the AChR surface. The α48–80 sequence neighbors with, and includes, residues α67–76, which are involved in formation of the MIR. The MIR is a relatively small surface area of the AChR that dominates the antibody response in human MG and rodent EMG. The sequence region α101–154 includes a putative extracellular sequence region between two cysteine residues at positions 128 and 142, which must be at least partially exposed on the AChR surface because it is glycosylated.

The amino-terminus of all AChR subunits is extracellular, although it is not clear whether it is exposed on the AChR surface because it is accessible to the binding of antibody only after mild denaturation of the AChR. The fifth region, α403–407, includes both the carboxyl-terminal end of the α subunit (residues α428–437), which is hydrophilic and likely exposed on the extracellular surface, and the hydrophobic segment α409–427, which is believed to form a transmembrane α helix, called M4. Three other transmembrane segmrnts are believed to exit in α and in the other AChR subunits, called M1 (residues α211–236), M2 (residues α242–261), and M3 (residues α277–298). These putative transmembrane regions largely correspond to three peptides that were recognized by the CD4⁻ cells of MG patients; α214–234, α246–264, and α280–297. Hydrophobic sequences in the core of a protein may form epitopes and possibly universal immunodominant epitope sequences for human CD4+ T cells, provided that they are flanked by sequence loops exposed on the surface of the molecule and accessible to the processing enzymes.

Short-term polyclonal lines specific for the universal AChR sequence regions can be easily propagated in vitro by cycles of stimulation with synthetic AChR peptides. Given the short time of propagation and the limited potential for biased clonal selection, they should be representative of the clonal repertoire of the CD4+ cells recognizing epitopes within each immunodominant sequence region. Those lines were challenged with single residue-substituted analogues of the relevant immunodominant sequence regions to define the residues involved in formation of "universal" epitopes, to obtain clues about the clonality of the lines, and (if they are polygonal) to understand whether they recognize one epitope or different overlapping epitopes: the response to the peptide analogues of polyclonal lines recognizing overlapping epitopes would be abolished by substitutions of "core" residues, common to all epitopes, and only partially affected by substitutions of residues included in some, but not all, epitopes.

Four peptides forming universal epitopes, α48–67, α304–322, γ75–94, and γ321–340, were examined. In the same patient, the CD4+ T cells recognizing a given universal epitope were polyclonal and recognized overlapping epitopes: their response was abolished by some substitutions, identifying residues common to all epitopes within a given region, while other substitutions residues (but did not obliterate) the response, indicating residues included in some, but not all, epitopes recognized by the line. Comparison of the residues involved in epitope formation for different lines supported the conclusion that, within the 20-residue peptides that were investigated, the same sequence segment is involved in formation of universal epitope(s) in DR-discordant patients. Within region α48–67, the segment 55–63 contained most or all of the residues involved in T cell activation for all lines from two different patients (DR4/w53 and DR7/w53 restricted). Within the region α304–322, residues 311–318 were involved in formation of all or most of the epitopes recognized by four lines from two different patients, both DR4/w53 restricted. Epitope recognition by one line from each patient was susceptible to substitutions outside the segment α311–318. Within region γ75–9$^4$, the segment 76–88 contained all residues involved in epitope(s) formation for three different patients, restricted by DR2/w51 and DR1. Within region γ321–340, the segment 324–332 contained residues involved in epitope formation for three lines from two different patients, all restricted by DR2/w51.

Some AChR epitopes dominate also the sensitization of CD4+ cells in mice, and tolerization of the CD4+ cells recognizing even just one of those dominant epitopes can protect from development of EMG. On the other hand, other AChR sequences sensitize mouse CD4+ cells of lesser or no pathogenic potential, whose tolerization does not affect EMG development. To understand whether similar epitope-specific tolerization of pathogenic CD4+ cells could be suitable for the treatment of MG, it was determined whether the immunodominant universal sequences described above are recognized by CD4+ cells able to drive the synthesis of pathogenic antibodies.

The chimeric human-SCID mouse model of MG was used. The effects on appearance of human IgG, anti-AChR antibodies, and MG symptoms of engraftment into SCID mice of PBMC, CD4+-depleted PBMC from the same patient, or CD4+-depleted PBMC supplemented with a CD4+ line from the same patient that was specific for a given immunodominant universal epitope of the α subunit was determined. The lines were propagated by cycles of stimulations in vitro with the individual 20-residue synthetic peptides, corresponding to a given a subunit universal CD4+ epitope. As controls, DTD- or TTD-specific CD4+ lines from the same patients were used.

SCID mice engrafted with PBMC developed anti-AChR antibodies and myasthenic symptoms, while the mice engrafted with CD4+-depleted PBMC or with PBMC supplemented with CD4+ cell lines specific for DTD or TTD did not present myasthenic weakness. Addition to the CD4+-depleted PBMC of any (but one) of the CD4− cell lines specific for α subunit universal epitopes induced myasthenic weakness in 25–50% of the engrafted mice and appearance of human anti-AChR antibody in the serum and at the neuromuscular junction of most mice.

Those findings clearly demonstrate that most of the anti-AChR CD4+ T cells specific for the universal epitope of the α subunit can drive the synthesis of pathogenic anti-AChR antibodies that cause myasthenic weakness and strongly support an important role of those universal sequence regions in the pathogenesis of MG. Those results underline the usefulness of synthetic epitope sequences for the propagation and study of autoimmune CD4+ cells of pathogenic relevance.

IV. Preparation of the Peptides of the Invention

A. Nucleic Acid Molecules of the Invention

1. Sources of the Nucleic Acid Molecules of the Invention

Sources of nucleotide sequences from which a nucleic acid molecule encoding a peptide or variant thereof of the invention, or a variant thereof, include total or polyA+ RNA from any eukaryotic, preferably mammalian, cellular source from which cDNAs can be derived by methods known in the art. Other sources of DNA molecules of the invention include genomic libraries derived from any eukaryotic cellular source.

Sources of nucleotide sequences of viral vectors useful in gene therapy include RNA or DNA from virally-infected cells, plasmids having DNA encoding viral proteins, nucleic acid in viral particles and the like.

W Moreover, the present DNA molecules may be prepared in vitro, e.g., by synthesizing an oligonucleotide of about 100, preferably about 75, more preferably about 50, and even more preferably about 40, nucleotides in length, or by subcloning a portion of a DNA segment that encodes a particular peptide.

2. Isolation of a Gene Encoding a Peptide of the Invention

A nucleic acid molecule encoding a peptide of the invention can be identified and isolated using standard methods, as described by Sambrook et al., *Molecular Cloning: A Laboratory Manual*, Cold Spring Harbor, N.Y. (1989). For example, reverse-transcriptase PCR (RT-PCR) can be employed to isolate and clone a preselected cDNA. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, NY, 1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of a particular eukaryotic gene. One primer is prepared which is predicted to anneal to the antisense strand, and another primer prepared which is predicted to anneal to the sense strand, of a nucleic acid molecule which encodes the preselected peptide.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs. Alternatively, isolated gel-purified fragments may be directly sequenced.

As used herein, the terms "isolated and/or purified" refer to in vitro isolation of a DNA, peptide or polypeptide molecule from its natural cellular environment, and from association with other components of the cell, such as nucleic acid or polypeptide, so that it can be sequenced, replicated, and/or expressed. For example, an "isolated, preselected nucleic acid" is RNA or DNA containing greater than 9, preferably 36, and more preferably 45 or more, sequential nucleotide bases that encode at least a portion of a peptide of the invention, or a variant thereof, or a RNA or DNA complementary thereto, that is complementary or hybridizes, respectively, to RNA or DNA encoding the peptide, or polypeptide having said peptide, and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of an isolated nucleic acid molecule of the invention is RNA or DNA (e.g., SEQ ID NO:1) that encodes human AChR (SEQ ID NO:2), or a fragment or subunit thereof, and shares at least about 80%, preferably at least about 90%, and more preferably at least about 95%, contiguous sequence identity with the human AChR polypeptide.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 2, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

3. Variants of the Nucleic Acid Molecules of the Invention

Nucleic acid molecules encoding amino acid sequence variants of a peptide of the invention are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the preselected peptide.

Oligonucleotide-mediated mutagenesis is a preferred method for preparing amino acid substitution variants of a peptide. This technique is well known in the art as described by Adelman et al., *DNA*, 2, 183 (1983). Briefly, DNA is altered by hybridizing an oligonucleotide encoding the desired mutation to a DNA template, where the template is the single-stranded form of a plasmid or bacteriophage containing the unaltered or native DNA sequence. After hybridization, a DNA polymerase is used to synthesize an entire second complementary strand of the template that will thus incorporate the oligonucleotide primer, and will code for the selected alteration in the preselected DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153, 3 (1987). Thus, the DNA that is to be mutated may be inserted-into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the peptide, and the other strand (the original template) encodes the native, unaltered sequence of the peptide. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. Coli JM101.

For example, a preferred embodiment of the invention is an isolated and purified DNA molecule comprising a preselected DNA segment, e.g., having SEQ ID NO:1, encoding a peptide of human AChR, wherein the DNA segment has nucleotide substitutions which are "silent" (see FIG. 9). That is, when silent nucleotide substitutions are present in a codon, the same amino acid is encoded by the codon with the nucleotide substitution as is encoded by the codon without the substitution. For example, leucine is encoded by the codon CTT, CTC, CTA and CTG. A variant of SEQ ID NO:1 at the sixth codon in AChR (CTC in SEQ ID NO:1) includes the substitution of CTT, CTA or CTG for CTC. Other "silent" nucleotide substitutions in SEQ ID NO:1 which can encode a peptide having a sequence corresponding to a contiguous portion of SEQ ID NO:2 can be ascertained by reference to FIG. 9 and page D1 in Appendix D in Sambrook et al., *Molecular Cloning: A Laboratory Manual* (1989). Nucleotide substitutions can be introduced into DNA segments by methods well known to the art. See, for example, Sambrook et al., supra. Likewise, nucleic acid molecules encoding other mammalian, preferably human, or viral, peptides may be modified in a similar manner, so as to yield nucleic acid molecules of the invention having silent nucleotide substitutions, or to yield nucleic acid molecules having nucleotide substitutions that result in amino acid substitutions (see peptide variants hereinbelow).

4. Chimeric Expression Cassettes

To prepare expression cassettes for transformation herein, the recombinant or preselected DNA sequence or segment may be circular or linear, double-stranded or single-stranded. Generally, the preselected DNA sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least two different species, or comprises DNA from the same species, which is linked or associated in a manner which does not occur in the "native" or wild type of the species.

Aside from preselected DNA sequences that serve as transcription units for a peptide, or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers. "Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

5. Transformation into Host Cells

The recombinant DNA can be readily introduced into the host cells, e.g., mammalian, bacterial, yeast or insect cells by transfection with an expression vector comprising DNA encoding a preselected peptide by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. For mammalian gene therapy, it is desirable to use an efficient means of precisely inserting a single copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is related to a DNA sequence which is resident in the genome of the host cell but is not expressed, or not highly expressed, or, alternatively, overexpressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding the peptide, which host cell may or may not express significant levels of autologous or "native" polypeptide.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described hereinabove to identify agents falling within the scope of the invention.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the peptide products of the introduced preselected DNA sequences or evaluating the phenotypic changes brought about by the expression of the introduced preselected DNA segment in the host cell.

B. Peptides. Peptide Variants, and Derivatives Thereof

The present isolated, purified peptides or variants thereof, can be synthesized in vitro, e.g., by the solid phase peptide synthetic method or by recombinant DNA approaches (see above). The solid phase peptide synthetic method is an established and widely used method, which is described in the following references: Stewart et al., *Solid Phase Peptide Synthesis*, W.H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2

(Academic Press, 1973), pp. 48–267; and Bavaay and Merrifield, "The Peptides," eds. E. Gross and F. Meienhofer, Vol. 2 (Academic Press, 1980) pp. 3–285. These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given peptide can be readily prepared. For example, amides of the peptide or peptide variants of the present invention may also be prepared by techniques well known in the art for converting a carboxylic acid group or precursor to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a peptide or peptide variant of the invention may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the peptide or peptide variants may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the peptide or peptide variant. Other amino-terminal modifications include aminooxypentane modifications (see Simmons et al., Science, 276, 276 (1997)).

In addition, the amino acid sequence of a peptide can be modified so as to result in a peptide variant (see above). The modification includes the substitution of at least one amino acid residue in the peptide for another amino acid residue, including substitutions which utilize the D rather than L form, as well as other well known amino acid analogs. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoyl-phenylalanine, phenylglycine, propargylglycine, sarcosine, and tert-butylglycine.

One or more of the residues of the peptide can be altered, so long as the peptide variant is biologically active. For example, it is preferred that the variant has at least about 10% of the biological activity of the corresponding non-variant peptide. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Conservative substitutions are shown in FIG. 10 under the heading of exemplary substitutions. More preferred substitutions are under the heading of preferred substitutions. After the substitutions are introduced, the variants are screened for biological activity.

Amino acid substitutions falling within the scope of the invention are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions peptide variants with non-conservative substitutions. Non-conservative substitutions entail exchanging a member of one of the classes described above for another.

Acid addition salts of the peptide or variant peptide, or of amino residues of the peptide or variant peptide, may be prepared by contacting the peptide or amine with one or more equivalents of the desired inorganic or organic acid, such as, for example, hydrochloric acid. Esters of carboxyl groups of the peptides may also be prepared by any of the usual methods known in the art.

V. Dosages, Formulations and Routes of Administration of the Peptides of the Invention The peptides or nucleic acid molecules of the invention, including their salts, are preferably administered so as to achieve a reduction in at least one symptom associated with a particular indication or disease, a decrease in the amount of antibody associated with the indication or disease, and/or a decreased responsiveness of CD4+ cells to the administered peptide or corresponding antigen. To achieve this effect(s), the peptide, a variant thereof or a combination thereof, agent may be administered at dosages of at least about 0.001 to about 100 mg/kg, more preferably about 0.01 to about 10 mg/kg, and even more preferably about 0.1 to about 5 mg/kg, of body weight, although other dosages may provide beneficial results. The amount administered will vary depending on various factors including, but not limited to, the agent chosen, the disease, the weight, the physical condition, and the age of the mammal, whether prevention or treatment is to be achieved, and if the agent is chemically modified. Such factors can be readily determined by the clinician employing animal models or other test systems which are well known to the art.

Administration of sense nucleic acid molecule may be accomplished through the introduction of cells transformed with an expression cassette comprising the nucleic acid molecule (see, for example, WO 93/02556) or the administration of the nucleic acid molecule (see, for example, Feigner et al., U.S. Pat. No. 5,580,859, Pardoll et al., Immunity, 3, 165 (1995); Stevenson et al., Immunol. Rev., 145, 211 (1995); Molling, J. Mol. Med., 75, 242 (1997); Donnelly et al., Ann. N.Y. Acad. Sci., 772, 40 (1995); Yang et al., Mol. Med, Today, 2, 476 (1996); Abdallah et al., Biol, Cell, 85, 1 (1995)). Pharmaceutical formulations, dosages and routes of administration for nucleic acids are generally disclosed, for example, in Feigner et al., supra.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

To prepare the composition, peptides are synthesized or otherwise obtained, purified and then lyophilized and stabilized. The peptide can then be adjusted to the appropriate concentration, and optionally combined with other agents. The absolute weight of a given peptide included in a unit dose of a tolerogen can vary widely. For example, about 0.01 to about 10 mg, preferably about 0.5 to about 5 mg, of at least one peptide of the invention, and preferably a plurality of peptides specific for a particular antigen, each containing a universal and/or immunodominant epitope sequence, can be administered. A unit dose of the tolerogen is preferably administered either via a mucous membrane, e.g., by respiratory, e.g., nasal (e.g., instill or inhale aerosol) or genitourinary tract administration, or orally, although other routes, such as subcutaneous and intraperitoneal are envisioned to be useful to induce tolerance.

Thus, one or more suitable unit dosage forms comprising the therapeutic agents of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including oral, or parenteral, including by rectal, transdermal, subcutaneous, intravenous, intramuscular, intraperitoneal, intrathoracic, intrapulmonary and intranasal (respiratory) routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. Preferably, orally administered therapeutic agents of the invention are formulated for sustained release, e.g., the agents are microencapsulated. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the therapeutic agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydro-gel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For topical administration, the therapeutic agents may be formulated as is known in the art for direct application to a target area. Conventional forms for this purpose include wound dressings, coated bandages or other polymer coverings, ointments, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1–25% by weight.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

Preferably, the peptide or nucleic acid of the invention is administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific indication or disease. Any statistically significant attenuation of one or more symptoms of an indication or disease that has been treated pursuant to the method of the present invention is considered to be a treatment of such indication or disease within the scope of the invention.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Examples of such substances include normal saline solutions such as physiologically buffered saline solutions and water.

A preferred route of administration of the therapeutic agents of the present invention is in an aerosol or inhaled form. The agents of the present invention can be administered as a dry powder or in an aqueous solution. Preferred aerosol pharmaceutical formulations may comprise, for example, a physiologically acceptable buffered saline solution containing between about 0.1 mg/ml and about 100 mg/ml of one or more of the agents of the present invention specific for the indication or disease to be treated.

Dry aerosol in the form of finely divided solid peptide or nucleic acid particles that are not dissolved or suspended in a liquid are also useful in the practice of the present invention. Peptide or nucleic acid may be in the form of dusting powders and comprise finely divided particles having an average particle size of between about 1 and 5 μm, preferably between 2 and 3 μm. Finely divided particles may be prepared by pulverization and screen filtration using techniques well known in the art. The particles may be administered by inhaling a predetermined quantity of the finely divided material, which can be in the form of a powder.

Specific non-limiting examples of the carriers and/or diluents that are useful in the pharmaceutical formulations of the present invention include water and physiologically acceptable buffered saline solutions such as phosphate buffered saline solutions pH 7.0–8.0.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197–224, Butterworths, London, England, 1984).

Aerosol delivery systems of the type disclosed herein are available from numerous commercial sources including Fisons Corporation (Bedford, Mass.), Schering Corp. (Kenilworth, N.J.) and American Pharnoseal Co., (Valencia, Calif.).

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

The formulations and compositions described herein may also contain other ingredients such as antimicrobial agents, or preservatives. Furthermore, the active ingredients may also be used in combination with other therapeutic agents, for example, bronchodilators.

VI. Management of Antibody-Mediated Disease

To treat an undesirable antibody-mediated immune response, such as the one in MG patients, universal and/or immunodominant epitopes are identified. MG is a disease that is diagnosed after a full sensitization of CD4+ cell to the AChR has occurred, and the synthesis of anti-AChR antibodies is actively occurring. To enhance the efficacy of peptide-based therapies, plasmapheresis is used in combination with the peptide treatment. Plasmapheresis "clears" the antibodies from the patient's blood, and it is in most cases associated with the administration of an immunosuppressant such as azathioprine, to help decrease the activity of the pathogenic immune cells. Thus, the administration of a peptide of the invention in combination with pheresis and optionally an immunosuppressant may be useful to manage MG as such a method would result in a long lasting down regulation of the anti-AChR response, in both the CD4+ and the B cell compartments.

In hemophilia A patients, a treatment similar to that described above for MG could be used for patients that have already developed antibody inhibitors to factor VIII. Moreover, the existence of universal CD4+ epitopes on the factor VIII molecule would allow the use of these approaches for the prevention of inhibitor development. Furthermore, the identification of universal CD4+ epitope sequences for factor VIII would allow their use for nasal tolerization procedures that would be suitable both in the treatment of established factor VIII inhibitors and in the prevention of inhibitor development, by tolerizing or down regulating the priming and/or activity of the T helper clones potentially reactive to factor VIII sequences, prior to the first therapeutic exposure to factor VIII in infancy.

Even if no universal CD4+ epitope sequences were identified on a given antigen, i.e. if every patient had a unique CD4+ repertoire, the peptides of the invention can provide the basis for tolerization to a given antigen towards the therapy of an undesirable antibody response. In the case of established immune resistance to factor VIII, the CD4+ repertoire of each patient is determined prior to "customizing" the tolerizing treatment to the epitopes recognized by that particular patient. This can be accomplished in about 6–8 weeks, at an estimated cost of $20,000/patient. In contrast, the cost of immune tolerance induction using daily intravenous infusions of factor VIII over many months is about $250,000/year per patient.

The invention will be further described by, but is not limited to, the following examples.

EXAMPLE I

Prevention of Experimental Myasthenia Gravis by Nasal Administration of AChR T Epitope Sequences Materials and Methods Peptide Synthesis and Characterization. Three peptides, 19–20 residues in length, corresponding to residues 150–169, 181–200 and 360–378 of the TAChR α subunit (SEQ ID NO:3), were synthesized by methods described in Houghton (1985). An additional three 20 residue peptides were synthesized, corresponding to residues 271–290, 321–340, and 431–450 of diphtheria toxin (DTX). These peptides were shown to be highly and universally immunogenic for human CD4+ T cells (Yeh et al., 1990).

Purification and Preparation of *Torpedo calfornica* AChR. TAChR was purified from *Torpedo californica* electric organ as alkali-stripped TAChR-rich membrane fragments, and characterized as described previously (Bellone et al., 1991). The TAChR concentration was determined as α-bungarotoxin (αBTX) binding sites (Schmidt et al., 1973). The protein concentration was determined by the Lowry assay (Lowry et al., 1981). The TAChR preparations contained 3.8–5.8 nmols of αBTX binding sites/mg protein. The protein composition was assessed by sodium dodecylsulphate polyacrylamide gel electrophoresis (Laemmli, 1970). The preparations employed herein consistently showed only the four TAChR subunits as the main protein bands.

For use in cell cultures, the TAChR-rich membrane fragments were diluted in RPMI-1640, and sterilized by UV irradiation.

For immunization, TAChR-rich membrane fragments were solubilized in 1% Triton X-100 (Bellone et al., 1991), diluted to 0.5 mg/ml in PBS and stored at −80° C.

Mice and Induction of Tolerance. B6 mice were purchased from Jackson Laboratory (Bar Harbor, Me.) and housed at the animal facility of the University of Minnesota. After light anesthesia by i.m. injection of Ketaset (100 mg/kg; Alveco Co., Inc., Fort Dodge, Iowa), the mice received into both nostrils a total of 25 μl of PBS containing 50 μg of peptide Tα150–169, either alone or pooled with equimolar amounts of peptides Tαl 80–200 and Tα360–378 (referred to as "peptide pool" or "α pool"). The dose was based on the results of an experiment in which increasing amounts of peptide α150–169 were used (50 μg, 100 μg, 200 μg, 400 μg and 800 μg). The lowest dose (50 μg) afforded a satisfactory level of protection. The tolerogen was administered as a solution instilled into the nostrils, a method of delivery which allowed accurate administration of a defined amount of solution. Nasal delivery of either aerosol or liquid antigen solutions has been shown to have similar efficacy in suppressing the effects of subsequent immunizations (Al-Sabbagh et al., 1996; Kuper et al., 1992; Liu et al., 1993; Husby et al., 1994; Neutra et al., 1996; Abbas et al., 1996; Conti-Fine et al., 1996; Karpus et al., 1996; Dick et al., 1993).

In protocol A, peptides or peptide-free PBS were administered two weeks before the first TAChR immunization, and then three more times, on the same day as the three immunizations with TAChR (at one month intervals, see below). In protocol B, peptides or peptide-free PBS were administered weekly, starting two weeks before beginning of the immunization with TAChR, for a total of 14 treatments (two before and 12 during TAChR immunization).

Control mice received 25 μl of peptide-free PBS, or a pool of the three synthetic DTX peptides in PBS.

Immunizations. Eight-ten week old mice were immunized by subcutaneous injections, along the back and at the base of the tail, with solubilized TAChR (50 μg), peptide Tα150–169 (100 μg), or the peptide pool (100 μg of each peptide). The mice were boosted twice at 4 week intervals with the same amount of antigen. The antigen solutions (in 100 μl PBS) were emulsified with an equal volume of complete Freund's adjuvant (FA) for the first injection, and with incomplete FA for the boosts. Control mice were injected with PBS emulsified in the appropriate adjuvant.

Evaluation of the Clinical Symptoms of EMG. EMG symptoms were quantified by a forced exercise using the inverted hang technique, sensitized by administration of a minute amount of pancuronium bromide (0–03 mg/kg i.p.) just prior to the beginning of the test (Karachunski et al., 1995). The mice hang from a grid, and the time it takes for the mouse to release its hold and fall three times ("holding time") was measured. The test was performed on the day of the first nasal administration, on the day before each immunization, and 7–14 days after the third immunization, just before sacrificing the animal. This test is parametric, and gives a quantitative assessment of the severity of the weakness.

To verify the myasthenic nature of the weakness observed, mice with significant weakness were injected i.p. with the cholinesterase inhibitor edrophonium chloride (Reversol, Organon Inc., West Orange, N.J.). Reversol immediately improved the strength of the animals, and alleviated the paralysis of the most severely affected mice. The test was performed blindly, i.e., without knowledge of the treatment that the mouse had received.

The holding time of normal mice was 10.4±2.1 minutes (n=99). Mice with holding times of eight minutes or longer were considered normal, those with a holding time of more than four minutes but less than eight minutes were considered to have moderate symptoms, and those with a holding time of less than four minutes were considered severely affected. Mice that were paralyzed or had died of respiratory paralysis are represented in the figures as having a holding time of zero.

Lymphocyte Proliferation Assay. Seven-ten days after the last immunization, spleen T cells were purified from individual mice (Bellone et al., 1991). Irradiated (3000 rad) spleen cells from non-immunized mice were diluted in RPMI-1640 (Gibco, Grand Island, N.Y.) supplemented with 10% heat inactivated fetal calf serum (Gibco), 50 µM 2-mercaptoethanol, 1 mM L-glutamine, 10 mM Hepes, 1 mM sodium pyruvate, 100 U/ml penicillin and 100 µg/ml streptomycin (culture medium) and used as antigen presenting cells. The spleen T cells ($1\times10^6$cells/ml in culture medium, 100 µl/well) were seeded in triplicate in 96 flat-bottom well plates containing 100 µl of $5\times10^6$/ml antigen presenting cells. One of the following Ag was added: 10 µg/ml PHA (Sigma, St Louis, Mo.); 5 or 10 µg/ml TAChR; 5 or 10 µg/ml of the individual peptides; increasing concentrations of pooled DTX peptides (2.5–20 µg/ml of each peptide); or increasing concentrations of pooled DTX peptides (2.5–20 µg/ml of each peptide) plus 10 µg/ml TAChR. Controls were triplicate wells containing T and antigen presenting cells, without any antigen. After 4 days the cells were labeled for 16 hours with $^3$H-thymidine (1 µCi per well, specific activity 6.7 Ci/mmol, Dupont, Boston, Mass.) and harvested (Titertek, Skatron, Sterling, Va.). $^3$H-thymidine incorporation was measured by liquid scintillation. The data are represented as stimulation indexes (S.I.), namely the ratio between the c.p.m. obtained for a culture in the presence of a given stimulus, and the average c.p.m. obtained for the unstimulated cultures (blanks).

Determination of Cytokine Secretion in Response to TAChR by Mouse Spleen Cells in vitro. Seven-ten days after the last immunization, spleen cells were cultured as described above for the proliferation assay, using sextuplicate cultures, with and without 10 µg/ml TAChR. Controls were triplicate cultures for each mouse group that did not receive any stimulus. After 12, 24 and 48 hours the supernatants were harvested, and the IL-2 and IL-10 concentration was determined by capture ELISA using duplicate samples (Pharmigen, San Diego, Calif.). Anti-IL-2 and anti-IL-10 Ab, and recombinant IL-2 and IL-10 (Pharmigen), were employed as standards.

Effect of Pre-Incubation with IL-2 on the Response to TAChR by Mouse Spleen Cells in vitro. Spleen cells from mice tolerized to the α pool following protocol B, or sham-tolerized with PBS, and immunized with TAChR as described above, were incubated in vitro with or without 1 ng/ml of mouse recombinant IL-2 (Pharmigen) in TCM for 5 days in 25 ml flasks (Coming Costar, Cambridge, Mass.). The cells were then tested in the proliferation assay described above, using 5 and 10 µg/ml of TAChR.

Anti-AChR Antibody Assay. Sera was obtained from the mice after each clinical testing. The serum concentration of anti-TAChR antibody was measured by RIPA using TAChR solubilized in Triton X-100 and labeled by the binding of $^{125}$I-αBTX (Bellone et al., 1991). The antibody concentration is expressed as µM precipitated $^{125}$I-αBTX.

Statistical Analysis. The level of significance of the differences of the average responses between two groups was determined by two tailed students't test, using the program Excel.

Results

Distribution in the Respiratory Tract of Solutions Administered Nasally. To determine which parts of the mouse respiratory system came in contact with solutions given nasally, a solution of ethidium bromide was employed. Ethidium bromide is absorbed through the mucosal lining of the respiratory tract and fluoresces brightly under U.V. light. Two mice were anesthetized and 25 µl of a 4% ethidium bromide solution in PBS was instilled into the nostrils. Ten-fifteen minutes later the animals were sacrificed by cervical dislocation. Their nasal cavities, larynx, trachea, bronchi and lungs were dissected, washed in PBS and examined under U.V. light for ethidium bromide staining. The mouse nostrils, larynx and trachea were brightly stained by ethidium bromide administered by the same procedure employed to administer the peptide solutions. The staining was increasingly weaker in the bronchi, and only weak focal signals were present in the lung parenchyma.

T Cells from Mice Treated Nasally and immunized with TAChR Peptides Do Not Respond in vitro to the Peptides or to TAChR. To assess the effect of nasal treatment with synthetic TAChR peptides on the ability of CD4+ cells to become sensitized to the same peptides, three groups of mice were nasally administered peptide Tα150–169, the α pool (5.0 µg/peptide), or peptide-free PBS, following protocol A. The mice were immunized three times with the peptide(s) used for the tolerization procedure, administered as subcutaneous immunizing injections in adjuvant. Seven-ten days after the last immunization, the spleen T cells of two mice tolerized with peptide Tα150–169, four mice tolerized with the peptide pool, and two sham-tolerized mice, were tested for their proliferative response in vitro to the immunizing peptides and to the TAChR.

Figure 1B:
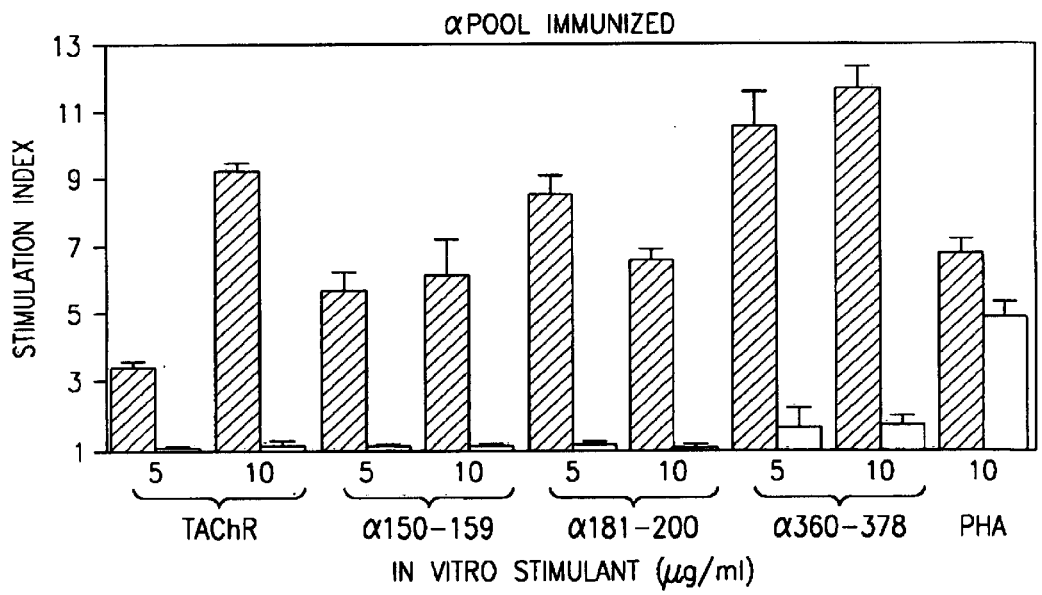

The results obtained within each group were highly consistent. FIG. 1 shows the results obtained with one mouse from each group. The T cells of sham-tolerized mice had a good proliferative response in vitro to the immunizing peptide(s) and to TAChR, indicating that they recognize epitopes similar to those originating from TAChR processing (Karachunski et al., 1995), while the T cells of peptide-tolerized mice did not respond to the immunizing peptides(s) or to TAChR.

Nasal Administration of Synthetic AChR Epitopes Prevents Appearance of EMG Symptoms. FIG. 2 summarizes the results obtained from testing the strength of mice treated nasally with the peptide epitopes and immunized with TAChR. Two groups of mice were studied. One group was treated with the TAChR peptide(s) using protocol A (panel A) while another group was treated with the peptides using protocol B (panel B). Sham-tolerized (panel "PBS") were employed as controls. For each group, the results obtained for the same mice prior to TAChR immunization (panel "naive") is also shown. The results depicted in FIG. 2 were obtained eight or ten weeks after beginning the immunization, when the maximum frequency of EMG symptoms was detected. The results from the two time points were consistent.

In agreement with previous studies which found variable EMG frequency (20–70%) in TAChR immunized B6 mice (Conti-Fine et al., 1997), the frequency of EMG in the sham-tolerized groups varied. In one experiment, 17 of 19 (89%) mice developed EMG. In the experiments shown in FIG. 2, all five sham-tolerized mice, and five of the ten sham-tolerized mice, had EMG symptoms, respectively.

Figure 2A:
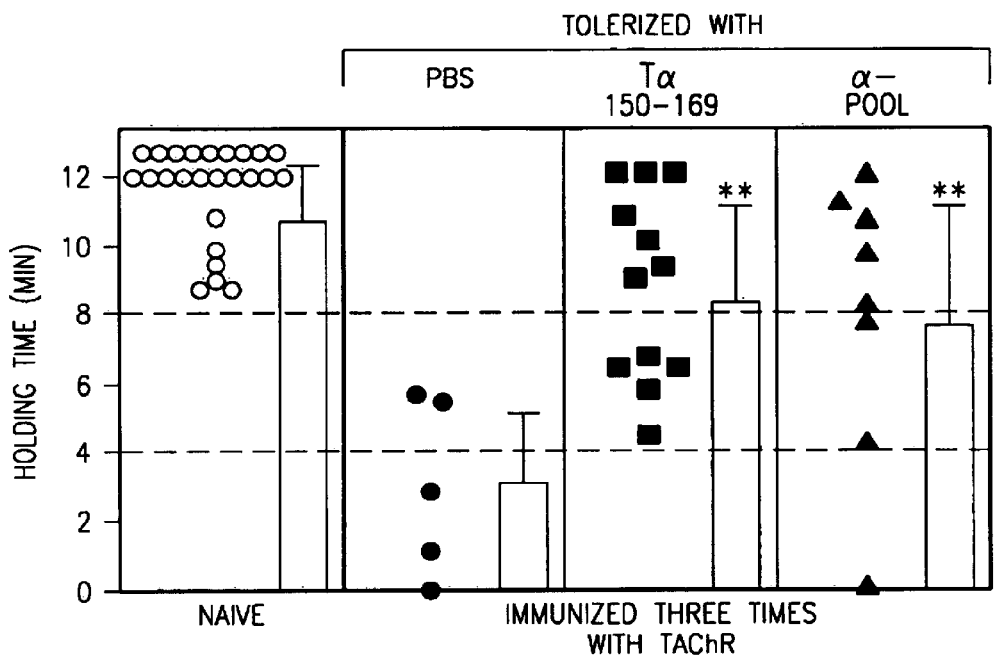
FIGS. 2A–B. Nasal administration of synthetic TAChR CD4+ epitope peptides inhibits EMG. Peptide Tα150–169, α pool or peptide-free PBS was administered nasally twice prior to immunization with TAChR, and at different time intervals during the course of the immunization (monthly, FIG. 2A; weekly, FIG. 2B). Three immunizations with 50 µg of TAChR, one month apart, were also administered. The data depict the muscle strength of the mice after the third TAChR injection. Muscle strength is measured as holding time using the curare sensitized hanging test described hereinbelow (see Example I). "normal" mice were mice having a holding time of eight minutes or more; moderately sick mice were those with holding times between four and eight minutes; and severely sick mice were those with holding times of less than four minutes. The four and eight minute levels are indicated by dashed horizontal lines. The panel marked "naive" depicts the values obtained for the mice prior to immunization with TAChR. The other plots depict the results obtained for mice sham-tolerized with PBS or mice tolerized with peptide Tα150–169 or with α pool, as indicated above the plots. The average holding time± S.D. of the different groups is indicated, as is the level of significance of the difference compared to the sham-tolerized group (**P<0.002; *P<0.02).
Figure 2B:
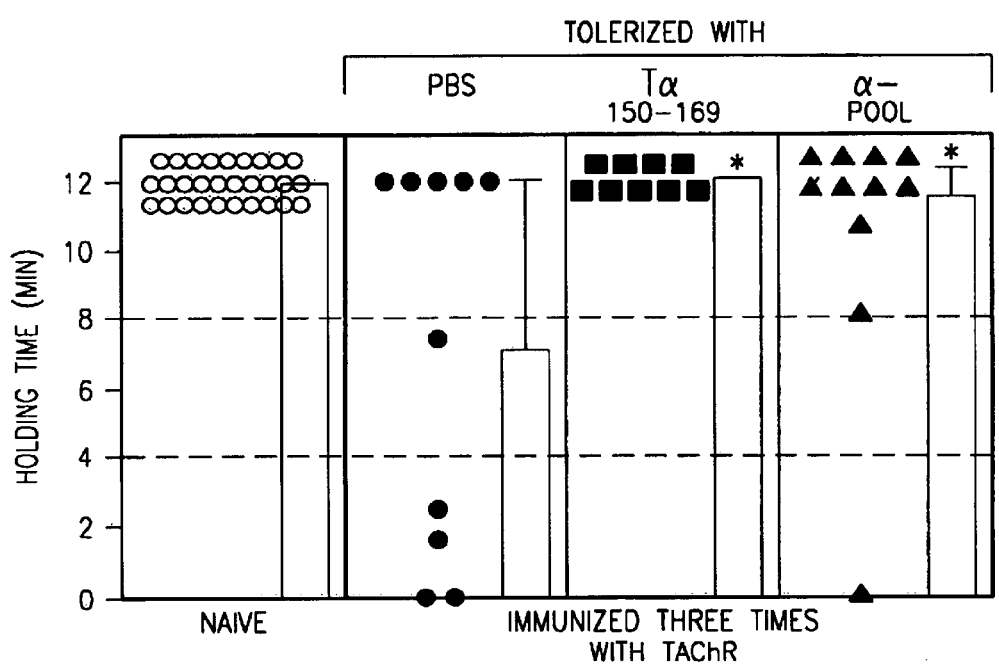
Figure 3A:
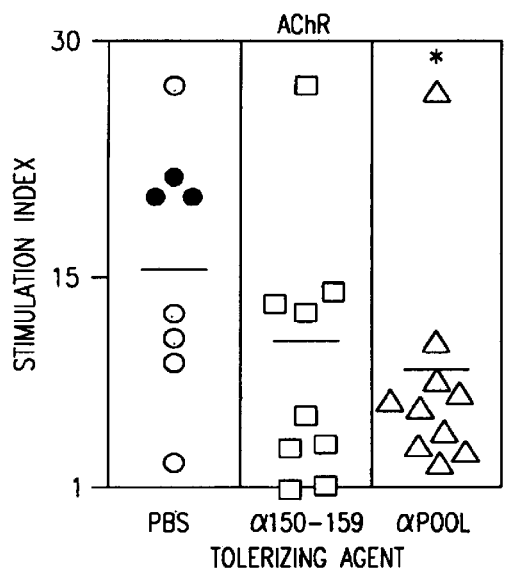
FIGS. 3A–D. Spleen T cells from mice treated nasally with synthetic TAChR T epitope sequences and immunized with TAChR respond minimally to peptide α150–169 and respond to the TAChR to a lesser extent than the T cells from sham-tolerized controls. Mice received weekly nasal administrations of peptide-free PBS (circles), Tα150–169 (squares) or α pool (triangles) as indicated below of each plots, and were immunized three times with TAChR. The spleen T cells of individual mice were tested in proliferation assays with TAChR (FIG. 3A) or individual peptides, i.e., Tα150–169 (FIG. 3B), Tα181–200 (FIG. 3C) or Tα360–378 (FIG. 3D). The data are the average S.I.±S.D. of triplicate cultures. The c.p.m. in the absence of any stimulation were 190±88. The proliferative responses of mice that had EMG are indicated with black symbols. The average responses of the different groups, and the level of significance of the difference between peptide-tolerized and sham-tolerized mice, are shown (**P<0.01; *P<0.03).
Figure 3B:
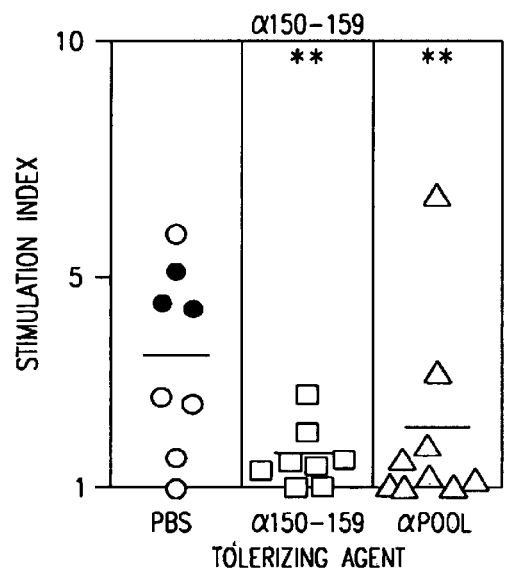
Figure 3C:
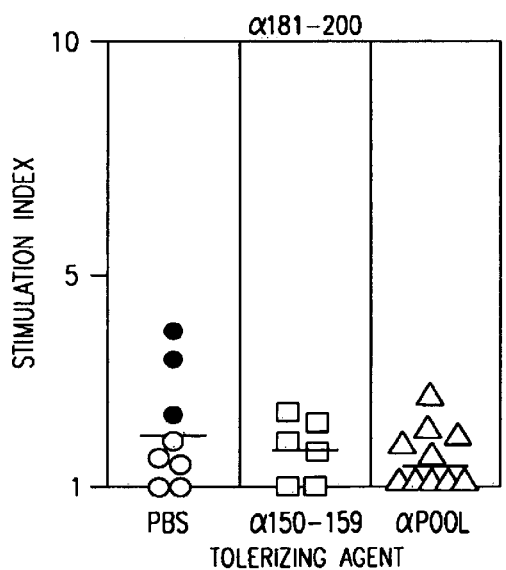
Figure 3D:
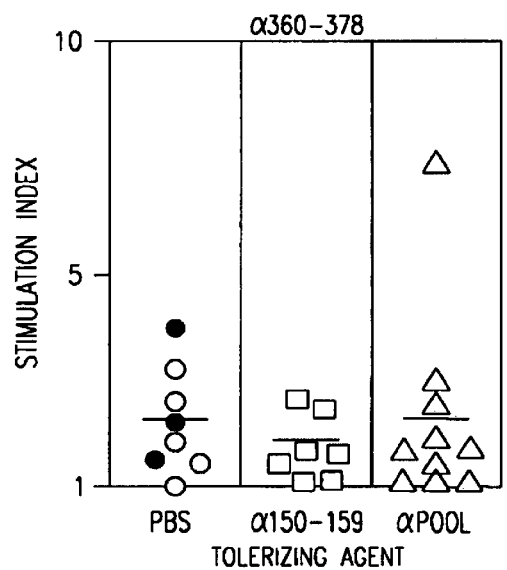

When the tolerizing peptides were administered following protocol A, five of the 12 mice (42%) tolerized with peptide Tα150–169, and three of the eight mice (37%) treated with the α pool, developed EMG, as compared to 100% of the mice sham-tolerized in parallel (FIG. 2A). When the tolerizing peptides were administered following protocol B, none of the mice that received nasal administration of peptide Tα150–169 had detectable weaknesses, and one mouse in the group treated with the peptide pool had a holding time barely below eight minutes at ten weeks. 50% of the sham-tolerized mice had EMG weakness (FIG. 2B).

In both experiments shown in FIG. 2, mice tolerized to peptide Tα150–169 and to the α pool had significantly longer holding times than the sham-tolerized mice.

Reduced T Cell Response to the Sequence Tα150–169 and to TAChR After Immunization With TAChR in Mice Treated Nasally With Peptide Tα150–169 or the α Pool. Mice used for the experiment shown in FIG. 2B were sacrificed ten weeks after beginning the TAChR immunizations. The spleen T cells of each mouse were tested in a proliferation assay with TAChR and the individual peptides Tα150–169, Tα181–200 and Tα360–378. FIG. 3 is organized in four panels, according to the challenging antigen used in the proliferation assay. Each panel summarizes the responses to the challenging antigen for sham-tolerized (PBS) mice, mice tolerized to α150–169 or mice tolerized to the α pool.

All but one of the sham-tolerized mice responded well to TAChR (S.I.=10–29). Two mice died of EMG before the experiment could be carried out. Most peptide-treated mice responded to TAChR: their average responses (horizontal bars in FIG. 3) were slightly lower then those of the sham-tolerized group. However, the difference was significant only for the mice tolerized to the α pool. All groups of mice treated nasally with TAChR peptides had lower proliferative responses to the TAChR than the control mice sham-tolerized in parallel, but the extent of the reduction varied in the different groups. The particular groups of peptide-tolerized mice shown in FIG. 3 are representative of those that had the least reduction in proliferative response to TAChR. In most other groups, the reduction was much more substantial, and some of the α pool -tolerized mice had barely detectable or no proliferative responses to TAChR (e.g., see FIGS. 5B and 6).

The T cells of most sham-tolerized mice responded to peptide Tα150–169 but to a much lesser extent than to TAChR, because the anti-TAChR CD4+ T cells of B6 mice recognize several epitopes on sequence regions other than Tα150–169 (Bellone et al., 1991). The T cells of both peptide-treated groups responded to Tα150–169 significantly less than the sham-treated mice. Several mice did not respond to Tα150–169 (S.I.<1.5).

Peptides Tα181–200 and Tα360–378, which are much less immunogenic for CD4+ cell sensitization than Tα150–169 (Karachunski et al., 1995), were recognized poorly even by the spleen T cells of sham-tolerized mice. Previous reports demonstrated that the T cell response of B6 mice to those epitope sequences can be detected only when using purified CD4+ cells instead of total spleen T cells (Bellone et al., 1991). The response to peptides Tα181–200 and Tα360–378 of the α pool-tolerized mice was the same as that of the control mice. Thus, the reduced T cell recognition of the TAChR molecule of the mice tolerized with the peptide pool is at least partially due to a reduced response to epitopes formed by the sequence Tα150–169.

The extent of the proliferative response to TAChR, Tα150–160 and Tα180–200 of the sham-tolerized mice correlated loosely with the presence of EMG symptoms. The three mice with EMG symptoms were among those with the highest S.I.

Figure 4A:
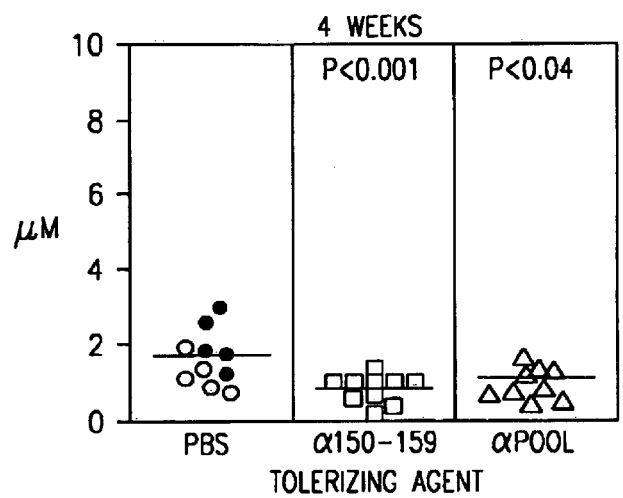
FIGS. 4A–C. Mice treated nasally with TAChR peptides have less serum anti-TAChR antibodies than sham-tolerized mice. The concentration of anti-TAChR antibodies in the sera of individual mice was determined at 4 (FIG. 4A), 8 (FIG. 4B) and 10 (FIG. 4C) weeks after the first TAChR immunization. Mice were tolerized by weekly inhalations (protocol B) of peptide Tα150–169 (squares), α peptide pool (triangles) or sham-tolerized with peptide-free PBS (circles), and immunized three times with TAChR, as indicated above the plots. The antibody concentration is expressed as µM precipitated $^{125}$I-α-bungarotoxin (BTX) binding sites. Mice that presented EMG symptoms are indicated by black symbols. The average antibody concentrations of the different groups and the level of significance of the difference between peptide-tolerized and sham-tolerized mice are indicated.
Figure 4B:
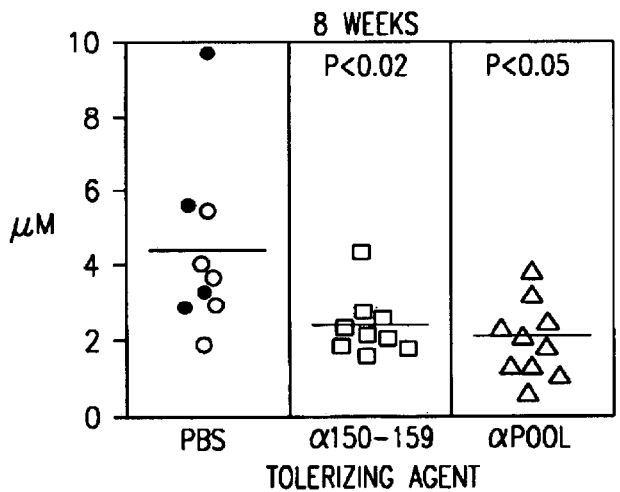
Figure 4C:
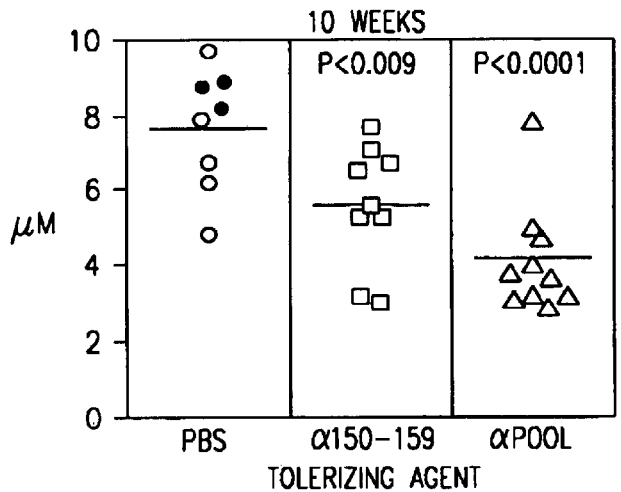

Nasal Treatment with AChR Peptides Causes Reduced Synthesis of TAChR Antibody. The serum anti-TAChR antibody concentration of individual mice tolerized with peptide Tα150–169, tolerized with the α pool or sham-tolerized, four, eight and ten weeks after the beginning of the immunization with TAChR was determined (FIG. 4). Mice treated with Tα150–169 or the α pool had significantly lower concentrations of anti-TAChR antibody than the sham-treated (PBS) group as early as 4 weeks after the first TAChR immunization, although they eventually developed substantial concentrations of anti-TAChR antibody (at ten weeks $5.5\pm1.5$ $\mu$M and $4.3\pm1.6$ $\mu$M vs. $7.2\pm1.8$ $\mu$M in the sham-tolerized group). The anti-TAChR antibody concentration of individual sham-tolerized mice correlated loosely with the presence of EMG symptoms, that is, mice with EMG symptoms were among those with the highest antibody concentrations (black symbols in FIG. 4).

Figure 5A:
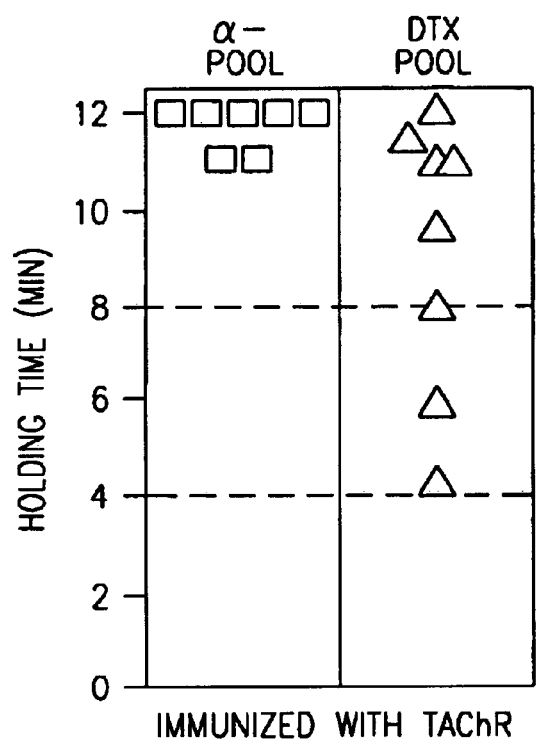
FIG. 5A) Muscle strength of individual mice. Mice were treated nasally with α pool or DTX peptides and their muscle strength measured after the third TAChR injection as described in the legend to FIG. 2. The 4- and 8-minute levels are indicated by dashed horizontal lines.
Figure 5B:
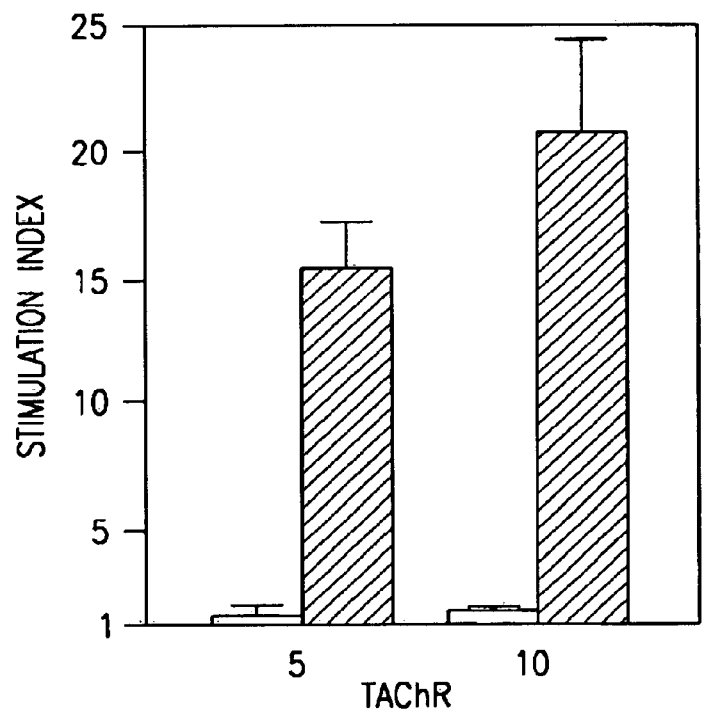
FIG. 5B) Proliferative response to TAChR (5 and 10 µg, as indicated) of triplicate cultures of pooled spleen T cells of four mice from each group, after the third TAChR immunization (white columns, α-pool treated mice; hatched columns, DTX peptide treated mice). The columns represent average S.I.±S.D. of triplicate cultures. The c.p.m. in the absence of any stimulation were 228±29 for the DTX peptide-tolerized mice, and 190±17 for the α-pool tolerized mice.

Nasal Administration of Synthetic DTX Peptides Does Not Affect the Anti-AChR T and Antibody Responses, or Development of EMG. To test the specificity of the effects observed after nasal administration of TAChR epitope peptides, the effects on the anti-TAChR response and appearance of EMG after nasal administration of three DTX peptides were tested. The DTX peptides are highly immunogenic for human CD4+ cells (Raju et al., 1995), and were of the same length and synthesized by the same procedure as the TAChR epitope sequences. The peptides were administered following protocol B. At the same time, two other groups of mice were sham-tolerized with PBS or tolerized with the α pool. None of the α-pool treated mice developed EMG, while the DTX peptide- and PBS-treated mice developed EMG with similar frequency (approximately 40%) (FIG. 5A). Mice treated nasally with DTX peptide or PBS developed similar serum anti-AChR antibody concentrations, which were higher than those of the AChR peptide-tolerized mice. After the third TAChR immunization, the spleen T cells of 4 mice from each group were pooled and tested for the proliferative response in vitro to TAChR. The spleen T cells from DTX peptide treated mice responded well to TAChR, while the responses of spleen T cells of the α pool treated mice were consistently very low (FIG. 5B).

Figure 6A:
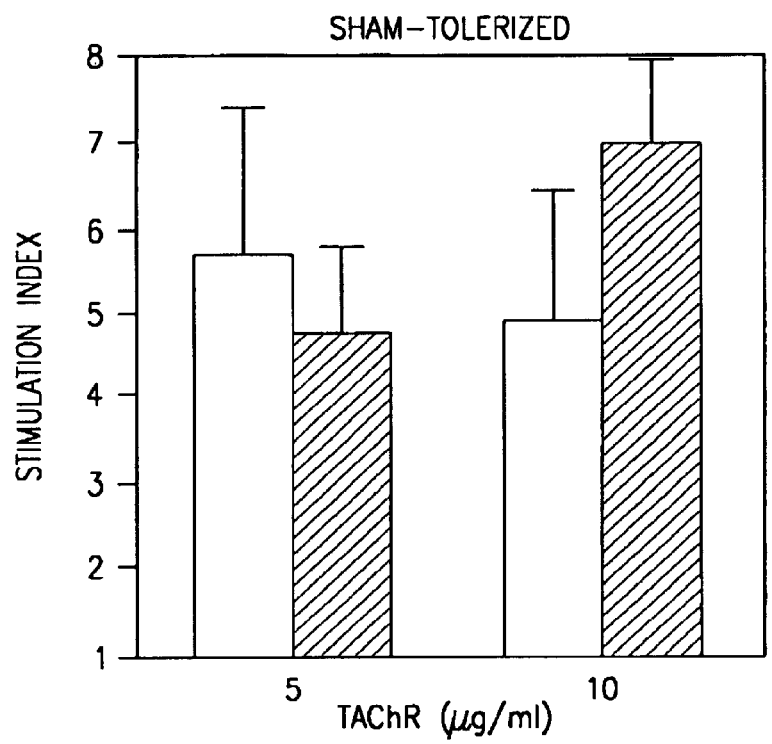
FIGS. 6A–B. The reduction of the in vitro response to TAChR of spleen T cells from AChR peptide-tolerized mice is reversed by IL-2 treatment. After the third TAChR injection, spleen T cells of mice sham-tolerized (FIG. 6A) or tolerized (FIG. 6B) with the α pool were pooled, incubated with (hatched columns) or without (white columns) IL-2, and tested in a proliferation assay for their response to TAChR. The columns represent average S.I.±S.D. of sextuplicate cultures. The c.p.m. in the absence of any stimulation were 410±124 for the sham-tolerized mice, and 366±78 for the (α pool-tolerized mice). The star indicates a significant difference of the proliferative response of cells treated with IL-2, as compared with the non treated cells (p<0.0001).
Figure 6B:
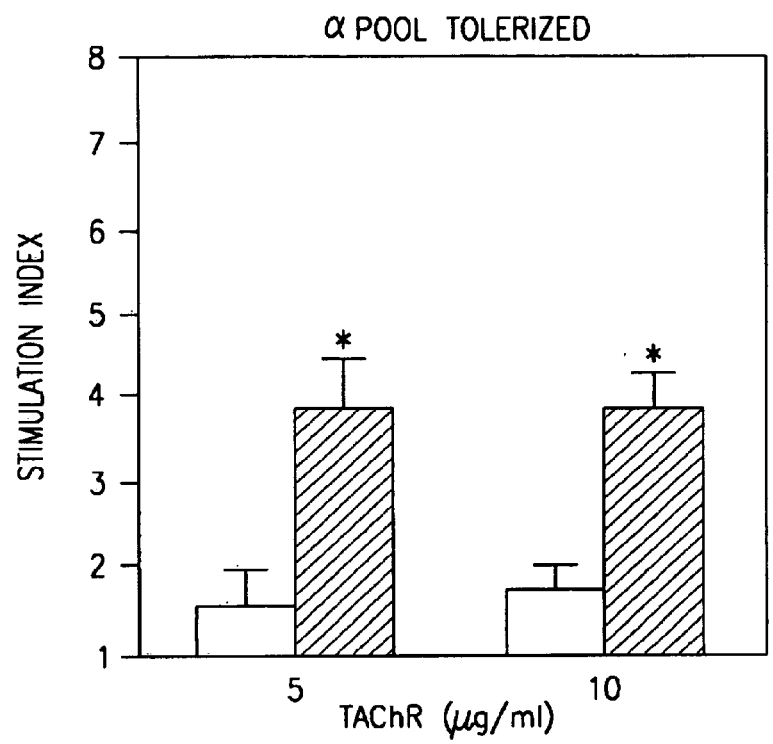

The Reduction of the in vitro Response to TAChR of Spleen T Cells from AChR Peptide-Tolerized Mice Is Reversed by IL-2. Anergy of antigen specific CD4+ T cells is a possible mechanism of T cell tolerization. A test for T cell anergy is a reversal of the nonresponsiveness in vitro to the antigen, by treatment of the T cells in vitro with IL-2 prior to antigen testing (DeSilva et al., 1991). Two groups of 4 mice each were treated nasally with PBS or with the α pool following protocol B. After the third TAChR injection, the spleen T cells of the mice of each group were pooled, cultured with or without IL-2 as described above, and tested in a proliferation assay for their response to TAChR. FIG. 6 depicts the average of the responses of sextuplets of identical cultures, obtained with the different T cells populations.

In the absence of IL-2 treatment, the spleen cells from a pool-tolerized mice responded to TAChR minimally, while those from sham-tolerized mice had a clear response. The IL-2 treatment did not affect the T cell response to TAChR of the sham-tolerized mice, while it increased substantially that of the α pool-tolerized mice.

Figure 7A:
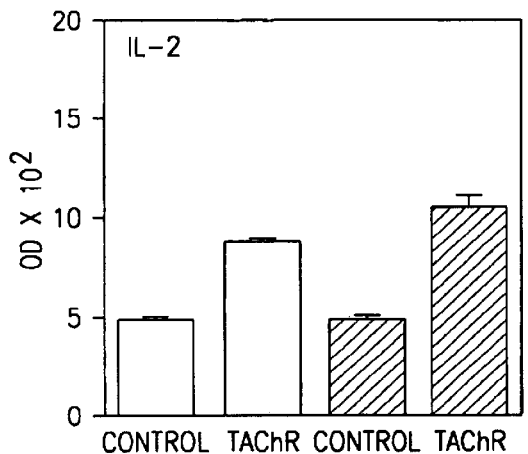
FIGS. 7A–B. Nasal treatment with AChR peptides stimulates AChR specific Th2 cells. Secretion of IL-2 (FIG. 7A) and IL-10 (FIG. 7B) in response to challenge with TAChR (10 μg) by pooled spleen T cells of 4 mice treated nasally (protocol B) with PBS (white columns) or a pool (hatched columns), after three TAChR injections. Controls were cultures that did not receive any stimulus. The columns represent the average (n=6) of the data obtained 24 hours after TAChR addition to the culture for IL-2, 48 hours for IL-10. The data are expressed as O.D. units detected in ELISA.
Figure 7B:
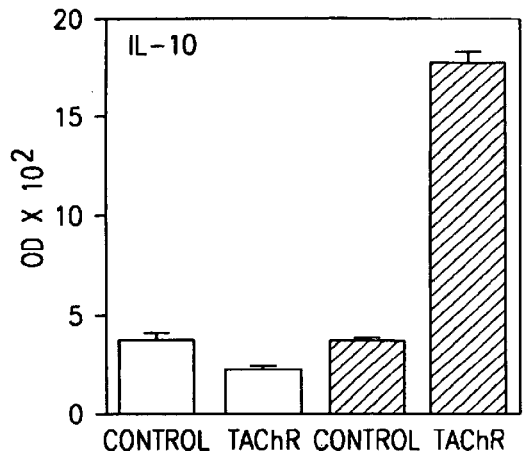

Nasal Treatment with AChR Peptides Stimulates AChR Specific Th2 Cells. Stimulation of modulatory Th2 cells is another possible mechanism of peripheral tolerance. To test this possibility, the secretion of IL-2 and IL-10 by spleen T cells in response to challenge with TAChR was determined. IL-2 and IL-10 are representative cytokines for Th1 and Th2 subsets, respectively. The same mice treated nasally with PBS or with α pool following protocol B were used for the IL-2 treatment experiments. After the third TAChR injection, the spleen T cells of 4 mice of each group were pooled and tested at different time intervals after addition of the TAChR for IL-2 and IL-10 secretion in the culture supernatant. The amount of IL-2 in the media was maximal 24 hours after AChR addition. IL-10 was maximal at 48 hours after AChR exposure. The average (n=6) of the data obtained at 24 hours for IL-2 and 48 hours for IL-10 are shown in FIG. 7. The presence of TAChR induced the same modest but significant increase of IL-2 secretion in the α pool and sham-tolerized groups. The presence of TAChR did not increase the IL-10 secretion by the T cells from the sham-tolerized mice, while it caused a large increase in the α pool-tolerized group.

Figure 8:
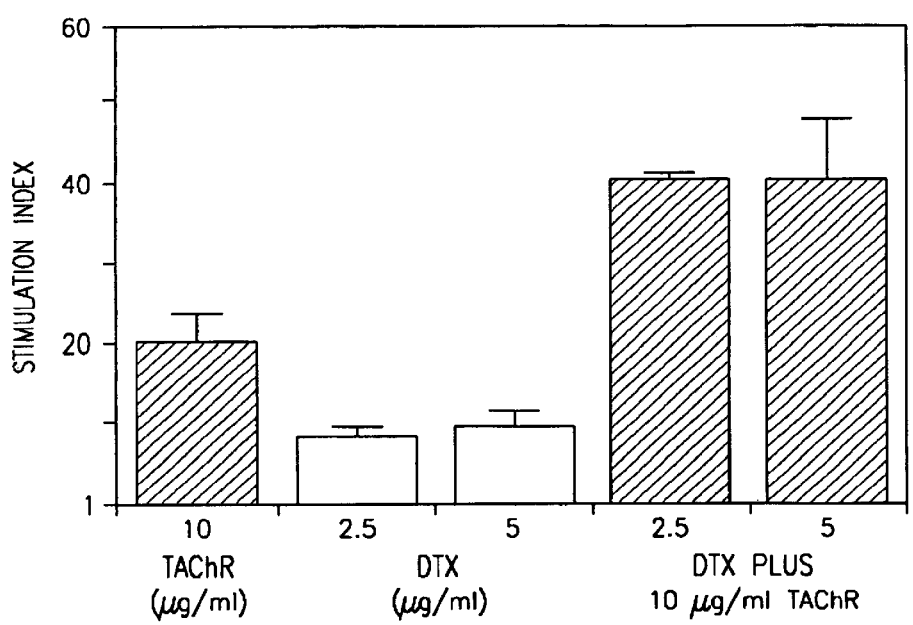
FIG. 8. The proliferative response to the TAChR of spleen T cells from TAChR immnunized mice is not affected by the presence in the culture of peptide specific immunoregulatory Th2 cells. Spleen T cells from mice treated nasally with DTX peptides and immunized three times with TAChR were tested in a proliferative assay with TAChR, with the DTX peptide pool (2.5 and 5 μg of each peptide), and with both TAChR and DTX peptides. The bar is the average S.I. of triplicate cultures. The c.p.m. in the absence of any stimulation were 149±97.

Reduced in vitro Response to the TAChR in α pool-tolerized Mice Is Not Due to the Presence in the Culture of Peptide Specific Immunoregulatory Th2 Cells. The reduced anti-AChR responses in vitro of the spleen T cells from TAChR peptide-tolerized mice could be due to immunoregulatory cytokines secreted in the culture medium by Th2 cells sensitized to the peptide(s) administrated nasally. The addition to T cell cultures of the tolerizing peptide together with the TAChR may cause a lesser proliferative response than that to the TAChR alone, because of peptide stimulated cytokine secretion by Th2 cells. As spleen T cells from α pool-tolerized mice had small and erratic proliferative responses to TAChR (see FIGS. 1, 3, and 5B), these cells could not be used. Thus, spleen T cells from mice treated with DTX peptides and immunized three times with TAChR were used. These T cells had a good proliferative response in vitro to TAChR, and a significant proliferative response to the DTX peptides, consistent with T cell sensitization resulting from nasal exposure to the DTX sequences (FIG. 8). When DTX peptide was used simultaneously with TAChR, the response obtained was significantly larger than that observed for each of two individual stimulants (FIG. 8), and corresponded reasonably well to the sum of the individual responses against TAChR and DTX peptides.

Discussion

Nasal administration of a 20 residue TAChR synthetic peptide, Tα150–169, that forms an immunodominant epitope recognized by pathogenic CD4+ cells, effectively protected B6 mice from induction of EMG caused by immunization with TAChR. The treatment was effective when administered prior to and during immunization with TAChR. Moreover, monthly or weekly administrations had comparable effects. This suggests that nasal administration did not cause further priming of pathogenic anti-AChR CD4+ T cells. Protection from EMG was associated with reduced T cell reactivity in vitro to the TAChR, reduced levels of anti-TAChR antibody in the blood, and minimal or absent proliferative response of spleen T cells to the immunodominant peptide Tα150–169. These effects were antigen-specific, since they could not be reproduced by nasal administration of a control peptide (a DTX peptide).

Although nasal administration of peptides Tα181–200 and Tα360–378 affected subsequent sensitization of T cells to all those sequences (FIG. 1), the protective effects on EMG induction are likely due to tolerization of CD4+ cells that recognize epitopes within the sequence Tα150–169, because nasal administration of peptide Tα150–169 alone was as effective as administration of the α pool in protecting from EMG and reducing the T and B cell responses to TAChR.

Since the AChR destruction and dysfunction that results in EMG symptoms is caused by antibody binding, it is likely that the altered anti-TAChR CD4+ reactivity after nasal tolerization results in protection from EMG because of a change in the anti-AChR antibody repertoire, due to preferential cooperation of different pairs of CD4+ helper T cells and B cells (Palmer et al., 1989; Myers, 1991; Bellone et al., 1994). To support this possibility, mice tolerized with TAChR peptides, while protected from EMG, developed substantial amounts of anti-AChR antibodies, but significantly lower than those observed for the mice sham-tolerized with peptide-free PBS (FIG. 4), or treated with DTX peptides. The pathogenic antibodies missing in the TAChR peptide-tolerized mice are likely synthesized with the help of CD4+ cells recognizing epitopes within the sequence Tα150–169. An important pathogenic role in mouse EMG of CD4+ cells recognizing epitopes within the sequence is supported by several findings: neonatal tolerization to this sequence region reduces susceptibility to EMG (Shenoy et al., 1993); B6 mice primed with AChR and boosted with a synthetic sequence α146–162 developed EMG while mice boosted with a control peptide did not (Shenoy et al., 1994); and in congenic B6 strains carrying the bm12 mutation of the I-A molecule, the ability by CD4+ cells to recognize this sequence correlates with propensity to EMG (Karachunski et al., 1995; Bellone et al., 1991; Infante et al., 1991). That CD4+ cells sensitized to a single dominant AChR epitope may drive the synthesis of pathogenic anti-AChR antibodies has been shown by transfer experiments for both rat (Yeh et al., 1990) and human (Conti-Fine et al., 1997) CD4+ lines against defined AChR epitopes.

Several mechanisms are involved in oral tolerance, including: anergy or deletion by apoptosis of antigen specific T cells, and induction of antigen specific regulatory CD4+ Th2 cells (Weiner et al., 1994; Chen et al., 1995). In EAE, it has been shown that the same CD4+ precursors can develop into regulatory Th2 cell if the antigen is administered orally, or into encephalitogenic Th1 cells if the antigen is administered subcutaneously in adjuvants (Chen et al., 1996). Antigen-specific regulatory CD4+ cells may exert a non-specific down regulating activity through secretion of cytokine, such as IL-4, IL-10, and TGF-β, that act on Th1 cells in topographic proximity, irrespective of their antigen specificity (antigen driven bystander suppression; Weiner et al., 1994).

Oral administration of an antigen can induce tolerance by different mechanisms, depending upon the dose of antigen that was fed (Friedman et al., 1994; Gregerson et al., 1993). Low doses of antigen generate Th2 regulatory cells, whereas high doses induce anergy (Friedman et al., 1994; Gregerson et al., 1993) and/or apoptosis of antigen-reactive Th1 and Th2 cells (Chen et al., 1995). Given the functional similarity of the lymphoid tissues associated with the respiratory and the gastrointestinal systems, similar mechanisms are likely involved in nasal tolerance (Kuper et al., 1992; Neutra et al., 1994).

Both clonal anergy and sensitization of regulatory Th2 cells seem to have occurred (FIGS. 6 and 7). High dose clonal deletion by apoptosis is less likely, since the highest doses used were as effective as the lowest (50 μg, i.e., 20 μmoles). This dose compares in weight to those used for low dose oral tolerance (Friedman et al., 1994). However, the molar concentrations employed in Friedman et al. were lower, as the antigen used in those studies had a higher molecular weight than the peptides employed herein. Epitope-specific anergy induction by nasal treatment with the TAChR peptides is directly supported by the finding that the reduced responsiveness in vitro of T cells to TAChR could be reversed by treatment with IL-2 (FIG. 6). Further circumstantial evidence for anergy of anti-Tα150–169 T cells is the finding that the proliferative response to the TAChR of the spleen T cells of mice tolerized to DTX epitopes and immunized to TAChR was not reduced by simultaneous stimulation of the T cells sensitized to the DTX peptides: the reduced proliferative response in vitro to Tα150–169 and to TAChR is unlikely due to the effects of cytokines released in the culture by Th2 cells.

Anergy or deletion of the T cells recognizing epitopes within the sequence Tα150–169 might suffice to protect from EMG, because, as discussed above, in B6 mice, the CD4+ cells that recognize epitopes within this sequence region are uniquely pathogenic. Also, the CD4+ response of B6 mice, which were hyperimmunized with TAChR and had a high frequency of EMG, focuses almost exclusively on the sequence Tα150–169, rather than spreading to other TAChR epitopes (Bellone et al., 1993). Thus, sensitization of CD4+ cells to epitopes within this sequence suffices to, and is prominent for, driving a pathogenic anti-TAChR antibodies response. This is different from EAE, where progression of the disease correlates with spreading of the CD4+ response to new epitopes within MBP and other myelin components (McRae et al., 1995).

Nasal administration of TAChR peptides sensitized AChR-specific Th2 cells, which were not detectable after TAChR immunization in mice sham-tolerized or tolerized to DTX peptides (FIG. 7). On the other hand, TAChR immunization per se appeared to sensitize Th1 cells only (FIG. 7). In MG, Th1 cells are likely involved in the pathogenic anti-AChR response. In EAE, Th1 cells are the direct effectors of demyelination, and their anergy or down regulation by Th2 subset directly affects their pathogenic action, and has therapeutic effects (Chen et al., 1994). On the other hand, in EMG, the protective effects of nasal administration of TAChR are indirect, and the procedures described herein will not have a therapeutic effect when the tolerogenic peptides are administered only after establishment of the pathogenic anti-TAChR antibody response. This is due to the long antibody life and the long life span of activated B cells (Gray, 1993) relative to the time frame of the experiments described herein.

The use of T cell epitope peptides instead of the whole antigen avoids the risk that the nasally administered antigen will prime synthesis of pathogenic antibodies. Even if nasal administration of peptides causes production of anti-peptide antibodies, they are extremely unlikely to cross-react with the cognate native antigen (Conti-Fine et al., 1996). Several studies have shown that (Conti-Fine et al., 1997) immunization with short TAChR peptides does not result in appearance of EMG. Moreover, short synthetic peptides are easily made.

Nasal tolerization using the approach described herein requires knowledge of the autoantigen sequences forming CD4+ epitopes. The CD4+ cells of most MG patients recognize a limited number of epitope sequences of the human AChR (Conti-Fine et al., 1997). Those sequence regions are recognized with high precursor frequency, and should therefore be considered both immunodominant and universal CD4+ epitopes. These epitopes are ideal candidates for application to human MG. The presence on a protein antigen of a few immunodominant, universal epitope sequences for sensitization of human CD4+ cells occurs also for the normal responses to exogenous antigen, like tetanus and diphtheria toxoid (Raju et al., 1995; Panina-Bordignon et al., 1989; Ho et al., 1990; Diethelem-Okita et al., 1997).

Although the procedure described here affects the anti-AChR antibody secreting B cells indirectly, and it does not have immediate therapeutic effects on established EMG, it also may be a viable candidate for MG management, if associated to plasmapheresis and azathioprine, which eliminate the existing anti-AChR antibodies and affect the activated B cells. The combined effects of such "two pronged" approach might result in a long lasting down regulation of the anti-AChR response, in both the CD4+ and the B cell compartments.

EXAMPLE II

Treatment of Factor VIII-Specific Disease

Approximately 25% of patients with severe hemophilia A develop blocking antibodies (inhibitors) to the missing coagulation factor, factor VIII (FVIII). Inhibitors block FVIII activity, and significantly compromise the ability to achieve therapeutic homeostasis during bleeding episodes. FVIII inhibitors also develop also during autoimmune hemophilia A, a rare but frequently fatal disease in which FVIII is the target of autoimmune response. FVIII inhibitors are high affinity IgG. Their synthesis requires the action of CD4+ T helper cells specific for FVIII.

A panel of about 240 synthetic peptides, 20 residues long and overlapping by 10 residues, spanning the FVIII sequence, is screened on T cells to determine which peptides have universal and/or immunodominant epitope sequences. The T cells are obtained from hemophilia A patients, autoimmune hemophilia patients, and healthy individuals that have a CD4+ response to FVIII. Identification of the CD4+ epitope repertoire on FVIII recognized by the patients or healthy individuals can be accomplished by using at least one of three sets of complimentary experiments, as follows: 1) Identification of the epitope repertoire of unselected CD4+ cells from the patient's blood by proliferation experiments using CD8+ depleted, CD4+ enriched peripheral blood lymphocytes (PBL), challenged with each individual peptide. 2) Identification of the CD4+ subset (Th1 or Th2) recognizing the different FVIII epitopes, by immunospot assays of the cytokines secreted by individual blood CD4+ cells in response to challenge with the difference FVIII peptides. Preferably, IL-2 and γ-interferon are employed to detect Th1 cells, and IL-4 is employed to detect Th2 cells. 3) Propagation of FVIII-specific CD4+ lines, by cycles of stimulation in vitro of the PBL with FVIII followed by IL-2 or IL4, and determination of their epitope repertoire and the Th1 or Th2 subset involved in the anti-epitope response, by challenging them with individual synthetic sequences in proliferation and immnunospot assays.

To identify the CD4+ epitope repertoire on FVIII in the hemophilia A mice (Bi et al., *Nature Genet.*, 10, 119(1995)), CD8+ depleted, CD4+ enriched spleen cells are employed instead of PBL. The mice have been injected with FVIII i.v. three times prior to spleen cell isolation, or by other routes that result in an immune response to FVIII. Alternatively, CD4+ cells are purified from the spleen and reconstituted with autologous antigen presenting cells. Peptides are screened by assays described herein to identify universal and/or immunodominant epitopes of FVIII. The C1 and the C2 domains of FVIII appeared to dominate the CD4+ response to FVIII of the mice. Once peptides having a universal and/or immunodominant epitope sequences are identified, they are administered nasally to hemophilia A mice prior to and during immunization with FVIII. Control mice are sham tolerized with peptide-free PBS. The effects of the tolerization on the antibody and CD4+ response to FVIII of the nasal administration of peptides is then determined.

Healthy humans have recurrent, transient sensitization of CD4+ cells to FVIII. This is likely due to extravasation of FVIII at sites, such as bruises, where FVIII sequence may be presented by professional antigen presenting cells, able to prime potentially autoreactive CD4+ cells specific for FVIII epitopes. In normal individuals, who have high blood levels of FVIII, the activated anti-FVIII CD4+ cells quickly disappear, possibly as a result of anergy or deletion by peripheral mechanisms of tolerance. Such cells persist in hemophilia A patients because their low FVIII levels, even after therapy, do not suffice for tolerization. Thus, the presence of anti-FVIII CD4+ cells in healthy humans can assist in the identification of universal CD4+ epitopes for FVIII.

A panel of overlapping peptides for FVIII were prepared which were 20 residues long, a length that compares with that of naturally processed class II restricted epitopes are peptides that are 9–14 residues long, and which overlapped by 10 residues. Thus, extra residues at either end of the peptide should not affect the peptide attachment to the binding cleft of the DR molecules, which is open at both ends. Moreover, the use of peptides of a length within the range of naturally processed peptides may result in the presentation of the specific epitope(s) without the need for processing, and may avoid the failure to stimulate the epitope-specific T cell to inappropriate peptide processing.

Figure 11:
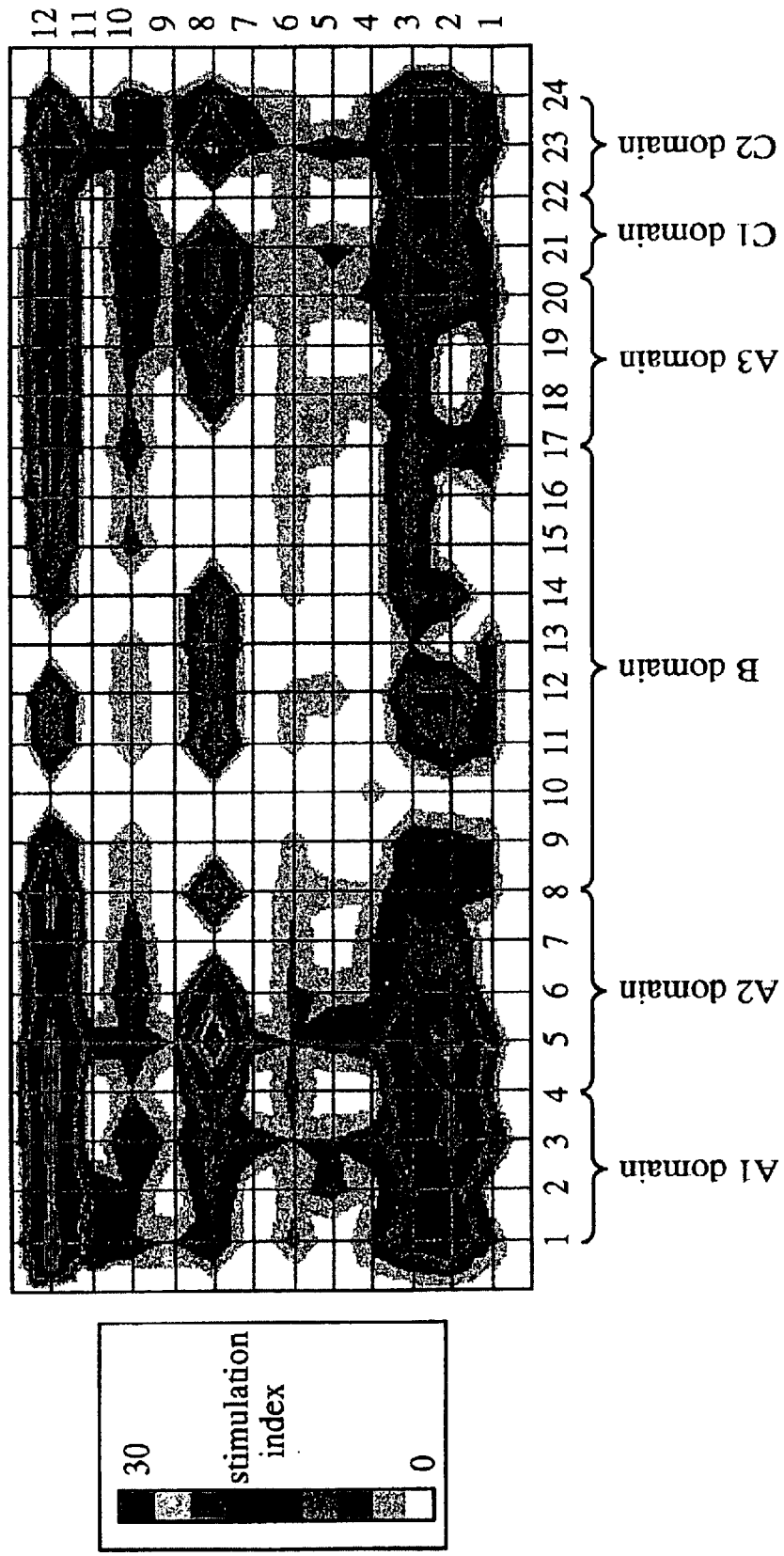
FIG. 11. Response of human T cells to factor VIII peptides.

The CD4+ cells from twelve healthy subjects were screened with a pool of FVIII peptides, e.g, 24 pools of 10 peptides each (FIG. 11). All subjects recognized one or more peptide pools. The pools comprising the sequence of the A2, A3 and C2 domains were recognized most strongly and most frequently. Anti-FVIII antibodies, including the inhibitors in hemophilia patients recognize primarily (but not exclusively) epitopes formed by the A2 and C2 domains. Thus, it appears that those domains may dominate both the pathogenic immune response to FVIII that leads to inhibitor formation in hemophilia A and the ephemeral, nonpathogenic responses of healthy subjects. Some subjects did not have a detectable response to the complete FVIII molecule, in spite of their significant response to one or more peptide pools. This is likely due to the much higher concentration of epitope sequences in the assays carried out with the peptides, than in those testing the response to FVIII.

References

Abbas, A. K., K. M. Murphy, and A. Sher. 1996. Functional diversity of helper T lymphocytes. *Nature* 383:787–793.

Al-Sabbagh, A., P. Nelson, Y. Akselband, R. Sobel, and H. Weiner. 1996. Antigen driven peripheral immune tolerance—suppression of experimental autoimmune encephalomyelitis and collagen-induced arthritis by aerosol administration of myelin basic protein or type II collagen. *Cell Immunol.* 171:111–119.

Akamizu, T., F. Matsuda, J. Okuda, H. Li, B. Kanda, T. Watanabe, T. Honjo and T. Mori. 1996. Molecular analysis of stimulatory anti-thyratropin receptor antibodies (TSAbs) involved in Graves' disease. *J Imrnunol.* 157:3148–3152.

Bellone, M., N. Ostlie, S. Lei, X-D. Wu, and B. Conti-Tronconi. 1991. The I-A bm12 mutation, which confers resistance to experimental myasthenia gravis, drastically affects the epitope repertoire of murine CD4+ cells sensitized to nicotinic acetylcholine receptor. *J. Immunol.* 147:1484–1491.

Bellone, M., N. Ostlie, S. Lei, and B. Conti-Tronconi. 1991. Experimental myasthenia gravis in congenic mice. Sequence mapping and H-2 restriction of T helper epitopes on the α subunits of *Torpedo californica* and murine acetylcholine receptors. *Eur. J. Immunol.* 21:2303–2310.

Bellone, M., N. Ostlie, P. Karachunski, A. Manfredi, and B. Conti-Tronconi. 1993. Cryptic epitopes on the nicotinic acetylcholine receptor are recognized by autoreactive CD4+ cells. *J. Immunol.* 151:1025–1038.

Bellone, M., P. Karachunski, N. Ostlie, S. Lei, and B. Conti-Tronconi. 1994. Preferential pairing of T and B cells for production of antibodies without covalent association of T and B epitopes. *Eur. J. Immunol.* 24:799–804.

Benjamini et al. (eds.), *Immnunology: A Short Course*, John Wiley & Sons, Inc., 3rd ed. (1996).

Chen, Y., V. K. Kuchroo, J. Inobe, D. A. Hafler, and H. L. Weiner. 1994. Regulatory T cell clones induced by oral tolerance: suppression of autoimmune encephalomyelitis. *Science* 265:1237–1240.

Chen, Y., J. Inobe, R. Marks, P. Gonnella, V. Kuchroo, and H. Weiner. 1995. Peripheral deletion of antigen-reactive T cells in oral tolerance. *Nature* 376:177–180.

Chen, Y., J. Inobe, V. Kuchroo, J. Baron, C. J. Janeway, and H. Weiner. 1996. Oral tolerance in myelin basic protein T-cell receptor transgenic mice: suppression of autoimmune encephalomyelitis and dose-dependent induction of regulatory cells. *Proc. Natl. Acad. Sci. USA* 93:388–391.

Conti-Fine, B. M, K. E. McLane, and S. Lei. 1996. Antibodies as a tool to study the structure of membrane proteins. The case of the nicotinic receptor. *Ann. Rev. Biophys. Biomol Struct.* 25:197–229.

Conti-Fine, B. M., M. P. Protti, M. Bellone, and J. F. Howard, Jr. 1997. Myasthenia Gravis: The Immunobiology of an Autoimmune Disease. R. G. Landes Company, Austin. 230pp.

DeSilva, D. R., Urdahl, K. B., and M. K. Jenkins. 1991. Clonal anergy is induced in vitro by T cell receptor occupancy in the absence of proliferation. *J. Immunol.* 147:3261–3267.

Dick, A., Y. Cheng, A. McKinnon, J. Liversidge, and J. Forrester. 1993. Nasal administration of retinal antigens suppresses the inflammatory response in experimental allergic uveoretinitis. A preliminary report of intranasal induction of tolerance with retinal antigens. *Brit. J. Ophthalmol.* 77:171–175.

Diethelem-Okita, B., R. Raju, D. Okita, and B. Conti-Fine. 1997. Epitope repertoire of human CD4+ T cells on tetanus toxin: identification of immunodominant sequence segmnents. *J. Infect. Dis.* 175:382–391.

Friedman, A., and H. L. Weiner. 1994. Induction of anergy or active suppression following oral tolerance is determined by antigen dosage. *Proc. Natl. Acad. Sci. USA* 91:6688–6692.

Genain, C. P., K. Abel, N. Belmar, F. Villinger, D. P. Rosenberg, C. Linington, C. S. Raine, and S. L. Hauser. 1996. Late complications of immune deviation therapy in a nonhuman primate. *Science* 274:2054–7.

Gray, D. 1993. Immunological memory. *Ann. Rev. Immunol.* 11:49–77.

Gregerson, D., W. Obritsch, and L. Donoso. 1993. Oral tolerance in experimental autoimmune uveoretinitis. Distinct mechanisms of resistance are induced by low dose vs. high dose feeding protocols. *J. Immunol.* 151:5751–5761.

Hashimoto, T. 1993. Cadherins and blistering skin diseases. *Curr. Opin. Dermatol.* 2, 244–249.

Ho, P., D. Mutch, K. Winkel, A. J. Saul, G. L. Jones, T. J. Doran, and C. M. Rzepczyk. 1990. Identification of two promiscuous T cell epitopes from tetanus toxin. *Eur. Immunol.* 20:477–483.

Houghten, R. 1985. General method for the rapid solid phase synthesis of large numbers of peptides: specificity of antigen-antibody interaction at the level of individual amino acids. *Proc. Natl. Acad. Sci. USA* 82:5131–5135.

Husby, S., J. Mestecky, Z. Moldoveanu, S. Holland, and C. Elson. 1994. Oral tolerance in humans. T cell but not B cell tolerance after antigen feeding. *Immunol.* 152:4663–4670.

Infante, A., P. Thompson, K. Krolik, and K. Wall. 1991. Determinant selection in murine experimental autoimmune myasthenia gravis: Effect of the bm12 mutation on T-cell recognition of acetylcholine receptor epitopes. *J. Immunol.* 146:2977–2982.

Karachunski, P., N. Ostlie, M. Bellone, A. Infante, and B. Conti-Fine. 1995. Mechanisms by which the I-A bm12 mutation influences susceptibility to experimental myasthenia gravis: a study in homozygous and heterozygous mice. *Scand. J. Immunol.* 42:215–225.

Karpus, W. J., K. J. Kennedy, W. S. Smith, and S. D. Miller. 1996. Inhibition of relapsing experimental autoimmune encephalomyelitis in SJL mice by feeding the immunodominant PLP 139–151 peptide. *Neuroscience Research* 45:410–423.

Kellermnan, S. D. McCormick, S. Freeman, John C. Morris and B. M. Conti-Fine. 1995. TSH receptor sequences recognized by CD4+ cells in Graves' disease patients and in healthy controls. *J. Autoimmunity* 8:685–698, 1995.

Kuper, C., P. Koornstra, D. Harneleers, J. Biewenga, B. J. Spit, A. M. Duijvestijn, P. J. van Breda Vriesman, and T. Sminia. 1992. The role of nasopharyngeal lymphoid tissue. *Immunol. Today* 13:219–224.

Laemmli, U. 1970. Cleavage of structural proteins during the assembly of the head of bacteriophage T4. *Nature* 227:680.

Liu, L., and G. G. MacPherson. 1993. Antigen acquisition by dendritic cells: intestinal dendritic cells acquire antigen administered orally and can prime naive T cells in vivo. *J. Exp. Med.* 177:1299–1307.

Lowry, O., N.,Rosebrough, A. Farr, and R. Randall. 1981. Protein measurement with Folin phenol reagent. *J. Biol. Chem.* 193:256.

Ma, C., G. Zhang, B. Xiao, J. Link, T. Olsson, and H. Link. 1995. Suppression of experimental autoimmune myasthenia gravis by nasal administration of acetylcholine receptor. *J. Neuroimmunol.* 58:51–60.

Manfredi, A. M. H. Yuen, L. Moiola, M. P. Protti and B. M. Conti-Tronconi. 1994. Human acetylcholine receptor presentation in Myasthenia Gravis: DR restriction of autoimmune T epitopes and binding of synthetic receptor sequences to DR molecules. *J. Immunol.* 152: 4165–4174.

Matzinger, P. 1994. Tolerance, danger, and the extended family. *Ann. Rev. Immunol.* 12:991–1045.

McRae, B., C. Vanderlugt, M. Dal Canto, and S. Miller. 1995. Functional evidence for epitope spreading in the relapsing pathology of experimental autoimmune encephalomyelitis. *J. Exp. Med.* 182:75–85.

Memar, B. Christensen, S. Raiararnan, R. Goldblum, K. Tyring, M, M. Brysk, D. J. McCormick, H. El Zaim, J-L. Pan and B. S. Prabhakar. 1996. Induction of blister-causing antibodies by a recombinant full-length, but not the extracellular, domain of the pemphigus vulgetris antigen (Desmoglein 3). *J. Immunol.* 157:3171–3177.

Metzler, B., and D. C. Wraith. 1993. Inhibition of experimental autoimmune encephalomyelitis by inhalation but not oral administration of the encephalitogenic peptide: influence of MHC binding affinity. *Int. Immunol.* 5:1 159–1169.

Miller, A., O. Lider, O. Abramsky, and H. L. Weiner. 1994. Orally administered myelin basic protein in neonates primes for immune responses and enhances experimental autoimmune encephalomyelitis in adult animals. *Eur. J. Immunol.* 24:1026–32.

Myers C. 1991. Role of B cell antigen processing and presentation in the humoral immune response. *FASEB* 5:2547.

Neutra, M., E. Pringult, and J. Kraehenbuhl. 1996. Antigen sampling across epithelial barriers and induction of mucosal immune response. *Ann. Rev. Immunol.* 14:275–300.

Nossal, G. 1995. Choices following antigen entry: antibody formation or immunologic tolerance? *Ann. Rev. Immunol.* 13:1–27.

Palmer, M, and Sercarz, E. 1989. Determinant preferences in the relationship between T and B cell specific for lysozyme. In: The Immune Response to Structurally Defined Proteins: The Lysozyme Model. S. Smith-Gill, E. Sercarz, editors. New York: Academic Press, pp. 285–321.

Panina-Bordignon, P., A. Tan, A. Termijtelen, S. Demotz, G. Corradin, A. Lanzavecchia. 1989. Universally immunogenic T cell epitopes: promiscuous binding to human MHC class II and promiscuous recognition by T cells. *Eur. J. Immunol.* 19:2237–2242.

Paul, *Fundamental Immunology*, 3rd ed., Raven Press (1993).

Plott, R. T. , M. Amagai, M. C. Udey and J. R. Stanley. 1994. Pemphigus vulgaris antigen lacks biochemical properties characteristic of classical cadherins. *J. Invest. Dermatol.* 17:168–172.

Raju R., D. Navaneetham, D. Okita, B. Diethellm-Okita, D. McCormick, and B. Conti-Fine. 1995. Epitopes for human CD4+ cells on diphtheria-toxin: structural features of sequence segments forming epitopes recognized by most subjects. *Eur. J. Immunol.* 25:3207–3214.

Raju, R., B. Diethelem-Okita, B., D. K. Okita, and B. M. Conti-Fine. 1996. Epitope repertoire of human CD4+ lines propagated with tetanus toxoid or synthetic tetanus sequences. *J. Autoimmunity* 9:79–88.

Schmidt, J., and M. Raftery. 1973. A simple assay for the study of solubilized acetylcholine receptors. *Anal. Biochem.* 52:349–354.

Shenoy, M., M. Oshima, M. Atassi, and P. Christadoss. 1993. Suppression of experimental autoimmune myasthenia gravis by epitope-specific neonatal tolerance to synthetic region alpha 146–162 of acetylcholine receptor. *Clin. Immunol. Immunopathol.* 66:230–238.

Shenoy, M., E. Goluszko, and P. Christadoss. 1994. The pathogenic role of acetylcholine receptor a chain epitope within α146–162 in the development of experimental autoimmune myasthenia gravis in C57B1/6 mice. *Clin. Immunol. Immunopathol.* 73:1–6.

Stanley, J. R. 1995. Autoantibodies against Adhesion Molecules and Structures in Blistering Skin diseases. *J. Experimental Medicine* 181:1–4.

Texier, B., C. Bedin, H. Taiig, L. Camoin, C. Laurent-Winter and J. Charreire. 1992. Characterization and sequencing of a 40-armino-acid peptide from human thyroglobulin inducing experimental autoimmune thyroiditis. *J. Immunol.* 148:3405–3411.

Wang, Z-Y., D. Okita, J. Howard Jr., and B. Conti-Fine. 1997. Th1 epitope repertoire on the alpha subunit of human muscle acetylcholine receptor in Myasthenia Gravis. *Neurology* 48:1643–1653.

Weetman, A. P. and A. M. McGregor. 1994. Autoimmune thyroid disease, Further developments in our understanding. *Endocrin. Rev.* 15: 788–830.

Weiner, H., A. Friedman, A. Miller, S. J. Khoury, A. Al-Sabbagh, L. Santos, M. Sayegh, R. B. Nussenblatt, D. E. Trenthan, and A. D. Hafler. 1994. Oral tolerance: immunologic mechanisms and treatment of animal and human organ-specific autoimmune diseases by oral administration of autoantigens. *Ann. Rev. Immunol.* 12:809–837.

Yeh, T. M., and K. A. Krolick. 1990. T cells reactive with a small synthetic peptide of the acetylcholine receptor can provide help for a clonotypically heterogeneous antibody response and subsequently impaired muscle function. *J. Immunol.* 144:1654–1660.

Yu, M., J. Johnson, and V. Tuohy. 1996. A predictable sequential determinant spreading cascade invariably accompanies progression of experimental autoimmune encephalomyelitis: a basis for peptide-specific therapy after onset of clinical disease. *J. Exp. Med.* 183:1777–1788.

Yuen, M. H., K. Macklin and Bianca M. Conti-Fine. 1996. MHC class II presentation of human acetylcholine receptor in Myasthenia Gravis. Binding of synthetic gamma subunit sequences to purified DR molecules. *J. Autommunity,* 9:67–77.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of preventing or inhibiting a pathological condition associated with aberrant, pathogenic or undesirable antibody production which is specific for a particular antigen that is normally expressed in a human, comprising: administering to the respiratory tract of a human afflicted with, or at risk of, the pathological condition a dosage form comprising an amount of at least one epitope peptide, wherein the administration of the dosage form is effective to reduce or inhibit the aberrant, pathogenic or undesirable antibody production in humans having divergent HLA haplotypes, wherein the sequence of the epitope peptide comprises a universal, immunodominant epitope, wherein the peptide comprises less than the sequence of the antigen, and wherein the antigen is an acetylcholine receptor or factor VIII.

2. The method of claim 1 wherein the administration is effective to reduce or inhibit the amount of said antibody for an antigen comprising said peptide.

3. The method of claim 1 wherein the antigen is factor VIII.

4. A method to tolerize a human to an antigen associated with aberrant, pathogenic or undesirable antibody production in the human, comprising: administering to the respiratory tract of the human at least one epitope peptide, having a universal immunodominant epitope sequence, wherein the administration is effective to tolerize CD4+ cells which are associated with antibody production to the antigen, in humans having divergent HLA haplotypes, wherein the peptide comprises less than the sequence of the antigen, and wherein the antigen is an acetylcholine receptor or factor VIII.

5. The method of claim 4 wherein the peptide is nasally administered.

6. The method of claim 1, or 4 wherein the administration does not increase synthesis of pathogenic antibody to the native antigen.

7. The method of claim 1 wherein the administration is effective to reduce or inhibit the affinity of the antibody for an antigen comprising said peptide.

8. The method of claim 7 wherein the antigen is factor VIII.

9. The method of claim 1 or 4 further comprising administering an agent that inhibits B cell activation.

10. The method of claim 4 wherein the antigen is factor VIII.

11. A method of preventing or inhibiting a pathological condition associated with aberrant, pathogenic or undesirable antibody production which is specific for a particular antigen that is normally expressed in a human, comprising: administering to the respiratory tract of a human afflicted with, or at risk of, the pathological condition a dosage form comprising an amount of at least one epitope peptide, wherein the administration of the dosage form is effective to reduce or inhibit the aberrant, pathogenic or undesirable antibody production in humans having divergent HLA haplotypes, wherein the sequence of the epitope peptide comprises a universal, immunodominant epitope, wherein the peptide comprises less than the sequence of the antigen, and wherein the peptide includes residues 150–169, 181–200 or 360–378 of the *Torpedo californica* acetylcholine receptor alpha subunit or a portion of those residues or corresponding residues in human acetylcholine receptor.

12. A method of preventing or inhibiting a pathological condition associated with aberrant, pathogenic or undesirable antibody production which is specific for a particular antigen that is normally expressed in a human, comprising: administering to the respiratory tract of a human afflicted with, or at risk of, the pathological condition a dosage form comprising an amount of at least one epitope peptide, wherein the administration of the dosage form is effective to reduce or inhibit the aberrant, pathogenic or undesirable antibody production in humans having divergent HLA haplotypes, wherein the sequence of the epitope peptide comprises a universal, immunodominant epitope, and wherein the peptide comprises less than the sequence of the antigen, wherein the antigen is factor VIII.

13. The method of claim 11 wherein the administration is effective to reduce or inhibit the amount of said antibody for an antigen comprising said peptide.

14. The method of claim 11 wherein the administration does not increase synthesis of pathogenic antibody to the native antigen.

15. The method of claim 11 wherein the administration is effective to reduce or inhibit the affinity of the antibody for an antigen comprising said peptide.

16. The method of claim 1, 3, 4, 8, 10 or 12 wherein the epitope peptide includes sequences from A2, A3 or C2 of factor VIII.

17. The method of claim 1, 4 or 12 wherein a pool of factor VIII peptides is administered.

18. The method of claim 17 wherein the pool includes sequences from A2, A3 or C2 of factor VIII.

* * * * *

UNITED STATES PATENT AND TRADEMARK OFFICE
CERTIFICATE OF CORRECTION

PATENT NO. : 6,929,796 B1
DATED : August 16, 2005
INVENTOR(S) : Conti-Fine

It is certified that error appears in the above-identified patent and that said Letters Patent is hereby corrected as shown below:

Title page,
Item [56], References Cited, FOREIGN PATENT DOCUMENTS, delete "H04K/7/00" and insert -- C07K/7/00 --, therefor.
OTHER PUBLICATIONS, "Hoyne, G.F., et al." reference, delete "response" and insert -- Responses --, therefor.

Column 57,
Line 58, after "antigen" delete ",".

Signed and Sealed this

Eighth Day of November, 2005

JON W. DUDAS
*Director of the United States Patent and Trademark Office*